(12) United States Patent
Cheng et al.

(10) Patent No.: US 11,305,021 B2
(45) Date of Patent: Apr. 19, 2022

(54) MEMBRANE-LYTIC BLOCK COPOLYMERS

(71) Applicant: UNIVERSITY OF WASHINGTON, Seattle, WA (US)

(72) Inventors: Yilong Cheng, Seattle, WA (US); Suzie H. Pun, Seattle, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 16/323,025

(22) PCT Filed: Aug. 4, 2017

(86) PCT No.: PCT/US2017/045566
§ 371 (c)(1),
(2) Date: Feb. 4, 2019

(87) PCT Pub. No.: WO2018/027164
PCT Pub. Date: Feb. 8, 2018

(65) Prior Publication Data
US 2019/0175752 A1 Jun. 13, 2019

Related U.S. Application Data

(60) Provisional application No. 62/371,163, filed on Aug. 4, 2016.

(51) Int. Cl.
| | | |
|---|---|---|
| A61K 47/69 | (2017.01) | |
| A61K 47/58 | (2017.01) | |
| A61K 38/10 | (2006.01) | |
| A61K 38/17 | (2006.01) | |
| C08L 33/12 | (2006.01) | |

(52) U.S. Cl.
CPC .......... *A61K 47/6907* (2017.08); *A61K 47/58* (2017.08); *A61K 38/10* (2013.01); *A61K 38/1761* (2013.01); *C08L 33/12* (2013.01)

(58) Field of Classification Search
CPC .... A61K 47/6907; A61K 47/58; A61K 38/10; A61K 38/1761; A61K 38/12
See application file for complete search history.

(56) References Cited

U.S. PATENT DOCUMENTS

| | | |
|---|---|---|
| 2003/0199090 A1 | 10/2003 | Monahan et al. |
| 2005/0191746 A1 | 9/2005 | Van et al. |
| 2007/0073014 A1 | 3/2007 | Kedar et al. |
| 2009/0048410 A1 | 2/2009 | Wakefield et al. |
| 2013/0266617 A1 | 10/2013 | Mirosevich et al. |
| 2013/0330278 A1* | 12/2013 | Gao .................. A61K 49/0082 424/9.6 |
| 2017/0246311 A1* | 8/2017 | Pun ........................ A61K 47/64 |

FOREIGN PATENT DOCUMENTS

| | | |
|---|---|---|
| WO | 2010021770 | 2/2010 |
| WO | WO 2010/054266 | * 5/2010 |
| WO | 2014066912 | 5/2014 |

OTHER PUBLICATIONS

Üzgün et al. (Biomacromolecules (2010) 11, 39-50).*
Wei et al. (Angew Chem. Int. Ed (2013), 52, 5377-5381).*
Jager et la. Polm. Chem., (2015), 6,4946-4954).*
Wong's Disertation (2008).*
Yuan et al. (JACS 2007, 129, 1717-1723).*
Adolph, et al., "Enhanced Performance of Plasmid DNA Polyplexes Stabilized by a Combination of Core Hydrophobicity and Surface PEGylation," Journal of Materials Chemistry B 2014, vol. 2, No. 46, pp. 8154-8164, 2014.
Behr, "The Proton Sponge: a Trick to Enter Cells the Viruses Did Not Exploit," CHIMIA International Journal for Chemistry, vol. 51, pp. 34-36, 1997.
Bennet, et al., "Polymer Nanoparticles for Smart Drug Delivery". Chapter 8: Application of Nanotechnology in Drug Delivery, ISBN: 978-953-51-1628-8, 2014.
Bergen, et al., "Analysis of the intracellular barriers encountered by ninviral gene carriers in a model of spatially controlled delivery to neurons," The Journal of Gene Medicine, vol. 10, pp. 187-197, 2008.
Butun, et al. "Selective betainisatin of tertiary amine methacrylate block copolymers" J. Mater. Chem., vol. 7, No. 9, pp. 1693-1695, 1997.
Chu, et al., "Application of Controlled Radical Polymerization for Nucleic Acid Delivery," Accounts Chem Res, vol. 45, No. 7, pp. 1089-1099, 2012.
Convertine, et al., "Development of a novel endosomolytic diblock copolymer for siRNA delivery," Journal of Controlled Release, vol. 133, pp. 221-229, 2009.
Davis, et al., "Evidence of RNAi in humans from systemically administered siRNA via targeted nanoparticles," Nature, vol. 464, pp. 1067-1070, 2010.
Du, et al., "Tailor-Made Dual pH-Sensitive Polymer-Duxorubicin Nanoparticles for Efficient Anticancer Drug Delivery," Journal of the American Chemical Society, vol. 133, No. 4, pp. 17560-17563, 2011.
El-Sayed, et al., "Smart polymeric carriers for enhanced intracellular delivery of therapeutic macromolecules," Expert Opinion Biological Therapy, vol. 5, No. 1, pp. 23-32, 2005.
Kay, "State-of-the-art gene-based therapies: the road ahead" Nature Review Genetics, vol. 12, pp. 316-328, 2011.
Kwon, et al., "A truncated HGP peptide sequence retains endosomolytic activity and improves gene delivery efficiencies," Molecular Pharmaceutics, vol. 7, No. 4, pp. 1260-1265, 2010.
Kwon, et al., "Application of an HIV gp41-Derived Peptide for Enhanced Intracellular Trafficking of Synthetic Gene and siRNA Delivery Vehicles," Bioconjugate Chemistry, vol. 19, pp. 920-927, 2008.
Lachelt, et al., "Nucleic Acid Therapeutics Using Polyplexes: A Journey of 50 Years (and Beyond)," Chemical Reviews, vol. 115, pp. 11043-11078, 2015.

(Continued)

Primary Examiner — Shirley V Gembeh
(74) *Attorney, Agent, or Firm* — Christensen O'Connor Johnson Kindness PLLC

(57) ABSTRACT

Membrane-lytic block copolymers, micellar assemblies, pharmaceutical compositions, and related methods are described.

21 Claims, 14 Drawing Sheets

Specification includes a Sequence Listing.

(56) References Cited

OTHER PUBLICATIONS

Lin, et al., "Degradable, pH-sensitive, membrane-destabilizing, comb-like polymers for intracellular delivery of nucleic acids" Biomaterials, vol. 31, No. 27, pp. 7150-7166, 2010.
Maier, et al., "An N-terminal domain of adenovirus protein VI fragments membranes by inducing positive membrane curavature," Virology, vol. 402, pp. 11-19, 2010.
Meyer, et al., "Breathing Life into Polycations: Funtionalization with pH-Responsive Endosomolytic Peptides and Polyethylene Glycol Enables siRNA Delivery," Journal of the American Chemical Society, vol. 130, pp. 3272-3273, 2008.
Meyer, et al., "Synthesis and Biological Evaluation of a Bioresponsive and Endosomolytic siRNA-Polymer Conjugate," Molecular Pharmaceutics, vol. 6, No. 3, pp. 752-762 2009.
Moyer, "Functional Genetic and Biophysical Analyses of Membrane Disruption oby Human Adenovirus," Journal of Virology, vol. 85, No. 6, pp. 2631-2641, 2011.
Murthy, et al., "Design and synthesis of pH-responsive polymeric carriers that target uptake and enhance the intracellular delivery of oligonucleotides," Journal of Controlled Release, vol. 89, p. 365-374, 2003.
Ogris, et al., "Melittin Enables Efficient Vesicular Escape and Enhanced Nuclear Access of Nonviral Gene Delivery Vectors," Journal of Biological Chemistry, vol. 276, No. 50, pp. 47550-47555, 2001.
Pinto-Gonzalez, et al., "Deoxyribonuclease II Is a Lysosomal Barrier of Transfection," Molecular Therapy, vol. 8, No. 6, pp. 957-963, 2003.
Rozema, et al., "Endosomolysis by Masking of a Membrane-Active Agent (EMMA) for Cytoplasmic Release of Macromolecules," Bioconjugate Chemistry, vol. 14, pp. 51-57, 2003.
Schellinger, et al. "Block copolymers containing a hydrophobic domain of membrane-lytic peptides form micellar structures and are effective gene delivery agents," ACS Macro Lett., vol. 2, No. 8, pp. 725-730, 2013.
Schellinger, et al., "Melittin-grafted HPMA-Oligolysine Based Copolymers for Improved Gene Delivery," Biomaterials, vol. 34, No. 9, pp. 2318-2326, 2013.
Schmaljohann, "Thermo- and pH-responsive polymers in drug delivery," Advanced Drug Delivery Reviews, vol. 58, pp. 1655-1670, 2006.
Suomalainen, et al., "A Direct and Versatile Assay Measuring Membrane Penetration of Adenovirus in Single Cells," Journal of Virology, vol. 87, No. 22, pp. 12367-12379, 2013.
Thomas, et al., "Enhancing polyethylenimine's delivery of plasmid DNA into mammalian cells," P Natl Acad Sci USA, vol. 99, No. 23, pp. 14640-14645, 2002.
Thomas, et al., "Progress and Problems With the Use of Viral Vectors for Gene Therapy," Nature Reviews Genetics, vol. 4, pp. 346-358, 2003.
Tosteson, et al., "The Sting Melittin Forms Channels in Lipid Bilayers," Biophysical Journal, vol. 36, pp. 109-116, 1981.
Van de Wetering, "2-(dimethylamino)ethyl methacrylate based (co)polymers as gene transfer agent," Journal of Controlled Release, vol. 53, pp. 145-153, 1998.
Varga, et al., "Quantitative comparison of polyethylenimine formulations and adenoviral vectors in terms of intracellular gene delivery processes," Gene Therapy, vol. 12, pp. 1023-1032, 2005.
Wagner, "Application of membrane-active peptides for nonvviral gene delivery," Advanced Drug Delivery Reviews, vol. 38, pp. 279-289, 1999.
Wang, et al., "A nanoparticle-based strategy for the imaging of a broad range of tumours by nonlinear amplification of microenvironment signals," Nature Materials, vol. 13, 204-212, 2014.
Wei, et al., "Dual Responsive, Stabilized Nanoparticles for Efficient In Vivo Plasmid Delivery," Chem Int Edit, vol. 52, pp. 5377-5381, 2013.
Whitehead, et al., "Knocking down barriers: advances in siRNA delivery," Nature Rewiews, vol. 8, pp. 129-138, 2009.
Wiethoff, et al., "Adenovirus membrane penetration: Tickling the tail of a sleeping dragon," Virology, pp. 479-480, 591-599, 2015.
Wiethoff, et al., "Adenovirus Protein VI Mediates Membrane Disruption following Capsid Disassembly," Journal of Virology, vol. 79, No. 4, pp. 1992-2000, 2005.
Won, et al., "Missing pieces in understanding the intracellular trafficking of polycation/DNA complexes," Journal of Controlled Release, vol. 139, pp. 88-93, 2009.
Wooddell, et al., "Hepatocyte-targeted RNAi Therapeutics for the Treatment of Chronic Hepatitis B Virus Infection," Molecular Therapy, vol. 21, No. 5, pp. 973-985, 2013.
Yin, et al., "Non-viral vectors for gene-based therapy," Nature Reviews Genetics, vol. 15, pp. 541-555, 2014.
Bütün, Vural et al. "Selective betainisation of tertiary amine methacrylate block copolymers" J. Mater. Chem (1997) vol. 7(9), pp. 1693-1695.
Schellinger, Joan G. et al. "Block copolymers containing a hydrophobic domain of membrane-lytic peptides form micellar structures and are effective gene delivery agents" ACS Macro Letter (2013) vol. 2(8), pp. 725-730.
The International Search Report (ISR) with Written Opinion for PCT/US2017/045566 dated Dec. 27, 2017, pp. 1-13.

* cited by examiner

MEMBRANE-LYTIC BLOCK COPOLYMERS

CROSS-REFERENCE TO RELATED APPLICATION

This application is a U.S. national phase of International Application No. PCT/US2017/045566, filed Aug. 4, 2017, which claims priority to U.S. Provisional Application No. 62/371,163, filed Aug. 4, 2016, both of which are incorporated by reference herein in their entirety.

STATEMENT REGARDING FEDERALLY SPONSORED RESEARCH

This invention was made with Government support under Grant No. R01 NS064404 awarded by the National Institutes of Health. The Government has certain rights in the invention.

BACKGROUND

The potentially transformative impact of intracellular drugs such as nucleic acid-based drugs, peptides and proteins has not been clinically realized primarily due to the considerable delivery challenges involved in intracellular delivery of macromolecular therapeutics. M. E. Davis et al. *Nature* 2010, 464, 1067-U1140; b) M. A. Kay, *Nat Rev Genet* 2011, 12, 316-328; c) K. A. Whitehead et al. *Nat Rev Drug Discov* 2009, 8, 129-138. For nucleic acids, two major classes of delivery vehicles, viral and non-viral systems, are used to package cargo and facilitate cell uptake but have their respective limitations. Viral vectors have immunogenicity and safety concerns and are expensive to manufacture. C. E. Thomas et al. *Nature Reviews Genetics* 2003, 4, 346-358. Non-viral vectors such as synthetic polymers have improved cost and safety profiles compared to viruses but are orders of magnitude less efficient at gene transfer compared to their viral counterparts. U. Lachelt et al. *Chem Rev* 2015, 115, 11043-11078.

Several studies investigating the intracellular trafficking of polymeric carriers have identified endosomal release to be the limiting step in intracellular delivery; if egress does not occur, endosomal contents are generally routed for lysosomal degradation. J. M. Bergen et al. *The Journal of Gene Medicine* 2008, 10, 187-197; b) C. M. Varga et al. *Gene Ther* 2005, 12, 1023-1032. Therefore, synthetic polymers have been designed to enhance endosomal release through mechanisms such as buffering in acidic pH (known as the "proton sponge effect") and incorporation of membrane-active peptides and alkylated carboxylic acid. J.-P. Behr, *CHIMIA International Journal for Chemistry* 1997, 51, 34-36; b) E. Wagner, *Advanced Drug Delivery Reviews* 1999, 38, 279-289; c) A. J. Convertine et al. *J Control Release* 2009, 133, 221-229; d) E. J. Adolph et al. *Journal of Materials Chemistry B* 2014, 2, 8154-8164. These approaches typically work well in cultured cells but may not translate easily for in vivo applications. Endosomal buffering by the proton sponge effect requires significant accumulated polymer concentrations that may be difficult to achieve in vivo. Meanwhile, membrane active peptides need to be shielded until reaching the endosome to minimize cell membrane disruption that results in off-site toxicity.

SUMMARY

The present disclosure provides a synthetic polymer that mimics the mechanism of efficient endosomal escape employed by adenovirus (Ad).

The main feature of the present disclosure is a block copolymer that comprises a primarily hydrophilic block that provides solubility in physiological conditions, and a second block that is pH-responsive and reversibly hydrophobic, to which is attached a membrane-lyric entity. At extracellular pH, the second block is hydrophobic, resulting in self-assembly of the hydrophobic block, reducing the lytic potential of the material before internalization. At certain acidic pH (that is encountered after internalization into the acidifying endosomes), the second block becomes hydrophilic and the membrane-lytic entity becomes exposed to facilitate endosomal release. The block copolymer may be associated with its macromolecular cargo by direct covalent attachment, or by non-covalent interactions (such as electrostatic binding, van der Waals, hydrogen bonding, hydrophobic encapsulation, etc.).

In one aspect, the present disclosure provides block copolymer comprising: a hydrophilic block comprising repeating units that are water-soluble at about neutral pH; and a pH-responsive block comprising repeating units that are hydrophobic at about neutral pH, wherein the pH-responsive block is covalently coupled a membrane-lytic entity.

In one aspect the present disclosure provides block copolymer comprising: a hydrophilic polyionic block comprising repeating units that are ionic at about neutral pH; and a pH-responsive block comprising repeating units that are hydrophobic at about neutral pH, wherein the pH-responsive block is covalently coupled a membrane-lytic entity.

In certain embodiments, the polyionic block comprises repeating units selected from repeating units that are cationic at about neutral pH, repeating units that are anionic at about neutral pH, and neutral hydrophilic repeating units.

In certain embodiments, the pH-responsive block is hydrophobic at pH of greater than about 6.8

In certain embodiments, the membrane-lytic entities are covalently linked to the pH-responsive block through a linker.

In the second aspect, the present invention provides a method for providing a copolymer according to any of the copolymers described further herein.

In a third aspect, the present invention provides micellar assembly comprising: a plurality of copolymers according to any of the copolymers described further herein. In certain embodiments, the micellar assembly has a diameter of about 5 nm to about 100 nm. In certain embodiments, the micellar assembly disassembles of pH of less than about 6.5.

In a fourth embodiment, the present invention provides a pharmaceutical composition comprising at least one of a block copolymer according to any aspect of this invention and a micellar assembly according aspect of this invention; and a therapeutic agent reversibly associated with the copolymer. In certain embodiments, the therapeutic agent is conjugated to the copolymer. In certain embodiments, the therapeutic agent is non-covalently associated with the copolymer. In certain embodiments, the therapeutic agent is a nucleic acid molecule. In certain embodiments, the therapeutic agent is a protein or peptide.

In a fifth aspect, the present invention provides a method of intracellularly delivering a nucleic acid, peptide or protein comprising: administering a pharmaceutical composition according to the present invention to a subject, wherein the pharmaceutical composition is endocytosed into the endosome and the pharmaceutical composition, thereby, releases the nucleic acid, peptide or protein from the endosome.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings.

FIG. 8 shows the relative YOYO-1 fluorescence intensity of CP and VIPER polyplexes at pH 7.4 and 5.7. The fluorescence intensity was normalized to the free DNA. Data are shown as mean±SD (n=3).

DETAILED DESCRIPTION

Figure 1:
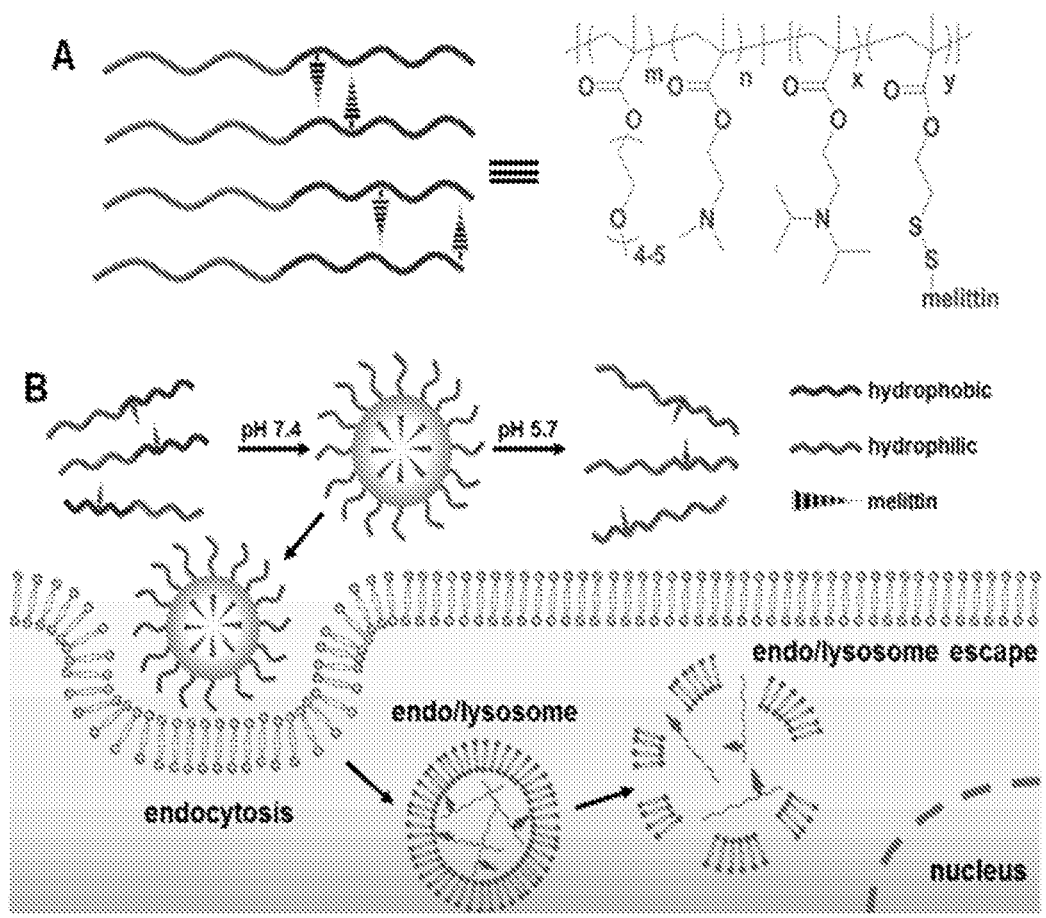
FIG. 1 shows A). Chemical structure of one embodiment of VIPER (virus-inspired polymer for endosomal release). B). Schematic illustration of VIPER-induced endo/lysosomal escape. At neutral pH, VIPER self-assembles into nanoparticles with membrane-lytic entity (in this example, the peptide melittin) restricted in the pH sensitive domain. After endocytosis by cells, the acidic endo/lysosome environment induces the hydrophilic phase transition of pDIPAMA, enabling melittin exposure, disruption of endo/lysosomal membrane, and endo/lysosomal escape.

In one aspect the present invention provides block copolymer comprising: a hydrophilic block that is water-soluble at about neutral pH; and a pH-responsive block comprising repeating units that are hydrophobic at about neutral pH, wherein the pH-responsive block is covalently coupled a membrane-lytic peptide.

At various places in the present specification, substituents of compounds of the disclosure are disclosed in groups or in ranges. It is specifically intended that the disclosure include each and every individual subcombination of the members of such groups and ranges.

It is further appreciated that certain features of the disclosure, which are, for clarity, described in the context of separate embodiments, can also be provided in combination in a single embodiment.

Conversely, various features of the disclosure which are, for brevity, described in the context of a single embodiment, can also be provided separately or in any suitable subcombination.

As used herein, the term "constitutional unit" of a polymer refers an atom or group of atoms in a polymer, comprising a part of the chain together with its pendant atoms or groups of atoms, if any. The constitutional unit can refer to a repeat unit. The constitutional unit can also refer to an end group on a polymer chain. For example, the constitutional unit of polyethylene glycol can be —CH$_2$CH$_2$O— corresponding to a repeat unit, or —CH$_2$CH$_2$OH corresponding to an end group.

As used herein, the term "repeat unit" corresponds to the smallest constitutional unit, the repetition of which constitutes a regular macromolecule (or oligomer molecule or block).

As used herein, the term "hydrophobic" refers to a moiety that is not attracted to water with significant apolar surface area at physiological pH and/or salt conditions. This phase separation can be observed via a combination of dynamic light scattering and aqueous NMR measurements. Hydrophobic constitutional units tend to be non-polar in aqueous conditions. Examples of hydrophobic moieties include alkyl groups, aryl groups, etc.

As used herein, the term "hydrophilic" refers to a moiety that is attracted to, and tends to be dissolved by water. The hydrophilic moiety is miscible with an aqueous phase. Hydrophilic constitutional units can be polar and/or ionizable in aqueous conditions. Hydrophilic constitutional units can be ionizable under aqueous conditions and/or contain polar functional groups such as amides, hydroxyl groups, or ethylene glycol residues. Examples of hydrophilic moieties include carboxylic acid groups, amino groups, hydroxyl groups, etc.

As used herein, the term "cationic" refers to a moiety that is positively charged, or ionizable to a positively charged moiety under physiological conditions. Examples of cationic moieties include, for example, amino, ammonium, pyridinium, imino, sulfonium, quaternary phosphonium groups, etc.

As used herein, the term "anionic" refers to a functional group that is negatively charged, or ionizable to a negatively charged moiety under physiological conditions. Examples of anionic groups include carboxylate, sulfate, sulfonate, phosphate, etc.

In certain embodiments, block copolymer of the present invention has a structure according to formula (I):

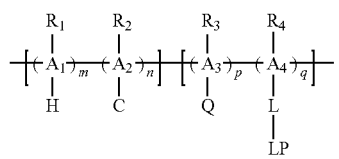

(I)

wherein $A_1$, $A_2$, $A_3$ and $A_4$ are selected from the group consisting of —C-C—, —C(O)(C)^C(O)O—, —O(C)$_a$C(O)- and —O(C)$_b$O—, wherein, a is 1-4, b is 2-4;

H is a hydrophilic moiety;

C is a charged moiety at pH about 7;

Q is hydrophobic at pH greater than about 7;

L is a linker;

LP is a membrane-lytic peptide;

$R_1$, $R_2$, $R_3$, and $R_4$ are independently selected from the group consisting of hydrogen, —CN, alkyl, alkynyl, heteroalkyl, cycloalkyl, heterocycloalkyl, aryl, and heteroaryl;

m is between 1-10,000;

n is between 1-10,000;

p is between 1-10,000; and q is between 1-10,000.

In certain embodiments, L is a disulfide bridge.

As used herein, the term "alkyl" refers to a saturated hydrocarbon group which is straight-chained (e.g., linear) or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. An alkyl group can contain from 1 to about 30, from 1 to about 24, from 2 to about 24, from 1 to about 20, from 2 to about 20, from 1 to about 10, from 1 to about 12, from 1 to about 8, from 1 to about 6, from 1 to about 4, or from 1 to about 3 carbon atoms.

As used herein, "alkylene" refers to a linking alkyl group.

As used herein, "alkenyl" refers to an alkyl group having one or more double carbon-carbon bonds. The alkenyl group can be linear or branched. Example alkenyl groups include ethenyl, propenyl, and the like. An alkenyl group can contain from 2 to about 30, from 2 to about 24, from 2 to about 20, from 2 to about 10, from 2 to about 8, from 2 to about 6, or from 2 to about 4 carbon atoms.

As used herein, "alkynyl" refers to an alkyl group having one or more triple carbon-carbon bonds. The alkynyl group can be linear or branched. Example alkynyl groups include ethynyl, propynyl, and the like. An alkynyl group can contain from 2 to about 30, from 2 to about 24, from 2 to about 20, from 2 to about 10, from 2 to about 8, from 2 to about 6, or from 2 to about 4 carbon atoms.

As used herein, "aryl" refers to monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "arylene" refers to a linking aryl group.

As used herein, "cycloalkyl" refers to non-aromatic carbocycles including cyclized alkyl, alkenyl, and alkynyl groups. Cycloalkyl groups can include mono- or polycyclic (e.g., having 2, 3 or 4 fused rings) ring systems, including spirocycles. In some embodiments, cycloalkyl groups can have from 3 to about 20 carbon atoms, 3 to about 14 carbon atoms, 3 to about 10 carbon atoms, or 3 to 7 carbon atoms. Cycloalkyl groups can further have 0, 1, 2, or 3 double bonds and/or 0, 1, or 2 triple bonds. Also included in the definition of cycloalkyl are moieties that have one or more aromatic rings fused (i.e., having a bond in common with) to the cycloalkyl ring, for example, benzo derivatives of pentane, pentene, hexane, and the like. A cycloalkyl group having one or more fused aromatic rings can be attached though either the aromatic or non-aromatic portion. One or more ring-forming carbon atoms of a cycloalkyl group can be oxidized, for example, having an oxo or sulfido substituent. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcamyl, adamantyl, and the like.

As used herein, "heteroalkyl" refers to an alkyl group having at least one heteroatom such as sulfur, oxygen, or nitrogen.

As used herein, "heteroalkylene" refers to a linking heteroalkyl group.

As used herein, a "heteroaryl" refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, "alkyl-" followed by a functional group refers to an alkyl group linking the functional group to the substituted compound. For example, "alkyl-aryl" refers to a substituent including an alkyl group linking an aryl group to the substituted compound. Exemplary "alkyl-aryl" groups include benzyl or phenethyl.

In certain embodiments, the hydrophilic polyionic block comprises repeating units that are cationic at about neutral pH. In certain further embodiments, such anionic repeating units are selected from the group consisting of 2-(dimethylamino)ethyl methacrylate, 2-dimethylaminoethyl acrylate, (3-acrylamidopropyl)trimethylammonium chloride, N-(3-aminopropyl) methacrylamide, N,N-diethylacrylamide, N,N-diethylmethacrylamide, N,N-dimethylacrylamide. N-[3-(dimethylamino)propyl]methacrylamide, 2-aminoethyl methacrylate, 2-(diethylamino)ethyl methacrylate, 2-(dimethylamino)ethylmethacrylate, [2-hydroxy-3-(2-aminoethyl) amino]propyl methacrylate, [3methacryloylamino) propyl]trimethylammonium chloride, and L-lysine.

In certain embodiments, the hydrophilic polyionic block comprises repeating units that are anionic at about neutral pH. In certain further embodiments, such anionic repeating units are selected from the group consisting of methacrylic acid, acrylic acid, dimethylmaleic anhydride modified N-(3-aminopropyl) methacrylamide, and 2-aminoethyl methacrylate.

In certain embodiments, the hydrophilic polyionic block comprises neutral hydrophilic repeating units. In certain further embodiments, the neutral hydrophilic repeating units are zwitterionic. In certain further embodiments, the neutral hydrophilic repeating units are selected from repeating units comprising oligo(ethylene glycol), hydroxypropylmethacrylamide, 2-hydroxyethyl methacrylate, N-isopropylacrylamide, 3-glucanoamidopropyl methacrylamide, 2-lactobionamidoethyl methacrylamide, betaine, phosphocholine, sulfobetaine, and carboxybetaine.

The block copolymers of the present invention comprise a pH-responsive block comprising repeating units that are hydrophobic at about neutral pH. In certain embodiments, the pH-responsive block is hydrophobic at pH of greater than about 7.0. In other embodiments, the pH-responsive block becomes hydrophobic above a pH that ranges from 4 to 7.2. In certain embodiments, the pH-responsive block comprises repeating units selected from the group consisting of 2-diisopropylaminoethyl methacrylate, 2-(pentamethyleneimino)ethyl methacrylate, 2-(hexamethyleneimino)ethyl methacrylate.

The block copolymers may comprise membrane-lytic entities covalently coupled to the pH-responsive block. In certain embodiments, the membrane-lytic entities are covalently linked to the pH-responsive block through a linker. In certain embodiments, the linker is selected from a carbon-carbon bond, an oligonucleotide, an ester-containing fragment, an amide-containing fragment, a disulfide-containing fragment.

The membrane-lytic entities are capable of lysing a cell membrane when present at critical concentrations. In certain embodiments, the membrane-lytic entity is selected from the group consisting of melittin, peptides from adeno virus protein VI, GALA, KALA, EGLA, JTS1, Gramicidin S, HGP peptide (sequence LLGRRGWEVLKYWWNLLQYWSQEL), sHGP peptide (sequence RGWEVLKYWWNLLQY), TAT peptide (sequence GRKKRRQRRRPQ), oligoarginine, and hemagglutinin.

In certain embodiments, block copolymer of the present invention has a structure according to formula (II):

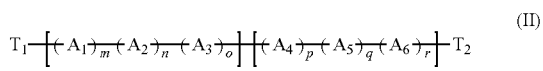

(II)

wherein
each $A_1$ is a hydrophilic monomer-derived unit;
each $A_2$ is a monomer-derived unit that is either independently neutral or charged at pH 10 or less;
each $A_3$ is a monomer-derived unit including a therapeutic peptide, nucleic acid, or nucleic acid derivative;
each $A_4$ is a monomer-derived unit with a pKa ranging from about pH 4 to about pH 7;
each $A_5$ is a monomer-derived unit including a therapeutic peptide, nucleic acid, or nucleic acid derivative;
$A_6$ is a monomer-derived unit including a membrane-lytic entity;
$T_1$ is independently absent or a targeting group;
$T_2$ is independently absent, a membrane-lytic entity, a therapeutic peptide, a nucleic acid or nucleic acid derivative;

m is from about 1 to about 10,000;
n is from about 0 to about 10,000;
o is from about 0 to about 10,000;
p is from about 1 to about 10,000;
q is from about 0 to about 10,000; and
r is from about 0 to about 10,000.

In certain embodiments, block copolymer of the present invention has a structure according to formula (IIa):

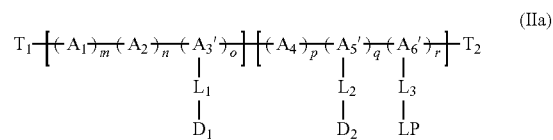

(IIa)

wherein
each $A_1$ is a hydrophilic monomer-derived unit,
each $A_2$ is a monomer-derived unit that is neutral or charged at pH of 10.0 or less;
each $A_4$ is a monomer-derived unit with a pKa ranging from about pH 4 to about pH 7;
each $A_3'$, $A_5'$ and $A_6'$ are independently

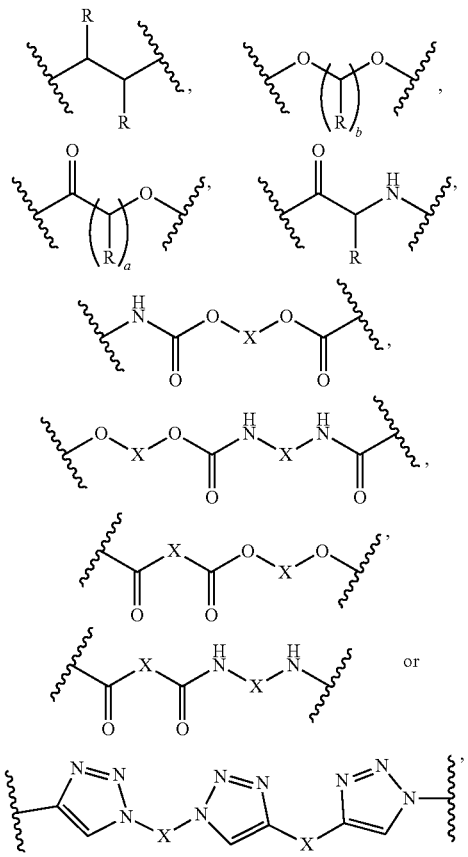

wherein
each X is independently comprises repeating units comprising an alkylene, arylene, disulfide, alkylene oxide or propane-2,2-diol;
wherein each X is optionally substituted with —$CO_2R^1$, $L_1$-$D_1$, $L_2$-$D_2$ or, $L_3$-LP, wherein $R^1$ is a hydrophilic group, each R is independently hydrogen, —CO$_2$R$^2$, —CN, alkyl, alkynyl, heteroalkyl, cycloalkyl, heterocycloalkyl, aryl or heteroaryl, where R$^2$ is a hydrophilic group, L$_1$-D$_1$, L$_2$-D$_2$ or, L$_3$-LP, a is 1-4, and b is 2-4;

each of L$_1$, L$_2$ and L$_3$ is independently absent or a linker;

each LP is a membrane-lytic entity;

each of D$_1$ and D$_2$ is independently a therapeutic peptide, nucleic acid, or nucleic acid derivative;

T$_1$ is independently absent or a targeting group;

T$_2$ is independently absent, a membrane-lytic entity, a therapeutic peptide, a nucleic acid or nucleic acid derivative;

m is from about 1 to about 10,000;

n is from about 0 to about 10,000;

o is from about 0 to about 10,000;

p is from about 1 to about 10,000;

q is from about 0 to about 10,000; and r is from about 0 to about 10,000.

In some embodiments, each A$_1$', A$_2$', A$_3$', A$_4$', A$_5$' and A$_6$' are independently

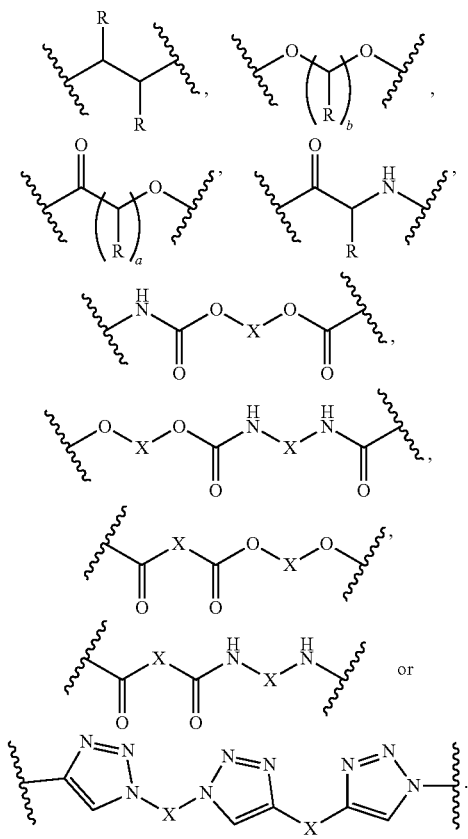

In some embodiments, each X independently comprises repeating units comprising an alkylene, arylene or alkylene oxide. In some embodiments, the alkylene oxide may be poly(ethylene oxide), poly(propylene oxide) or poly(butylene oxide). In other embodiments, disulfide, alkylene oxide or propane-2,2-diol. The disulfide may include include the structure

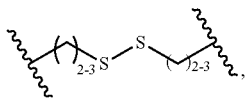

and the propane-2,2-diol may include the structure

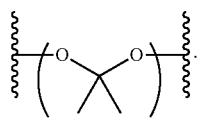

The number of repeating units in X may range from 1 to 30, 1 to 20, 1 to 15, 1 to 10, 5 to 30, 10 to 30 or 15 to 30.

In some embodiments, the hydrophilic group of R$^1$ and R$^2$ includes one or more alkene oxide units. For example, the hydrophilic group may include poly(alkene oxide), such as poly(ethylene oxide), poly(propylene oxide) or poly(butylene oxide). In some embodiments, the hydrophilic group of R$^1$ and R$^2$ may include an amino group, such as -alkyl-NR'.

In some embodiments, a is 2-4 or 1, 2, 3 or 4. In some embodiments, b is 2, 3 or 4.

In certain embodiments, the block copolymer of the present invention has a structure according to formula (II) where each of L$_1$, L$_2$ and L$_3$ independently comprise a covalent linkage connecting D$_1$, D$_2$ or LP to the polymer backbone, respectively. In some embodiments, L is a reversible linkage such as a disulfide bridge, hydrazine bond, boronic ester or peptide. In some embodiments, L$_1$, L$_2$ or L$_3$ is a disulfide bridge. In some embodiments, L$_1$, L$_2$ or L$_3$ is a peptide. In some embodiments, L$_1$, L$_2$ or L$_3$ is an irreversible bond, formed by, for example click chemistry or thiol-ene conjugation. In some, it can be reversible, like disulfide bridge, or hydrazone bond, or boronic ester. In other embodiments. L$_1$, L$_2$ or L$_3$ is absent.

In certain embodiments, the hydrophilic polyionic block (i.e., the block including A$_1$, A$_2$ and A$_3$) comprises repeating units that are cationic at about neutral pH. In certain further embodiments, such anionic repeating units are selected from the group consisting of 2-(dimethylamino)ethyl methacrylate, 2-dimethylaminoethyl acrylate, (3-acrylamidopropyl) trimethylammonium chloride, N-(3-aminopropyl) methacrylamide, N,N-diethylacrylamide, N,N-diethylmethacrylamide, N,N-dimethylacrylamide, N-[3-(dimethylamino)propyl]methacrylamide, 2-aminoethyl methacrylate, 2-(diethylamino)ethyl methacrylate, 2-(dimethylamino)ethylmethacrylate, [2-hydroxy-3-(2-aminoethyl) amino]propyl methacrylate, [3methacryloylamino) propyl]trimethylammonium chloride, and L-lysine.

In certain embodiments, the hydrophilic polyionic block comprises repeating units that are anionic at about neutral pH. In certain further embodiments, such anionic repeating units are selected from the group consisting of methacrylic acid, acrylic acid, dimethylmaleic anhydride modified N-(3-aminopropyl) methacrylamide, and 2-aminoethyl methacrylate.

In certain embodiments, the hydrophilic polyionic block comprises neutral hydrophilic repeating units. In certain further embodiments, the neutral hydrophilic repeating units are zwitterionic and selected from repeating units comprising betaine, phosphocholine, sulfobetaine, and carboxybetaine. In certain further embodiments, the neutral hydrophilic repeating units are selected from repeating units comprising oligo(ethylene glycol), hydroxypropylmethacrylamide, 2-hydroxyethyl methacrylate. N-isopropylacrylamide, 3-glucanoamidopropyl methacrylamide, and 2-lactobionamidoethyl methacrylamide.

Each $A_2$ of the block copolymer is a monomer-derived unit that is neutral or charged at pH 10 or less. For example, the monomer from which the monomer-derived unit is derived is neutral or charged at pH 10 or less. In some embodiments, each $A_2$ is a monomer-derived unit that is neutral or charged at pH 9.8 or less, or 9.6 or less, or 9.4 or less, or 9.2 or less, or 9.0 or less, or 8.8 or less, or 8.6 or less, or 8.4 or less, or 8.2 or less, or 8.0 or less, or 7.8 or less, or 7.6 or less, or 7.4 or less, or 7.2 or less, or 7.0.

The block copolymers of the present invention comprise a pH-responsive block (i.e., the block including $A_4$, $A_5$ and $A_6$). The pH-responsive block includes repeating units that are hydrophobic at about neutral pH (e.g., $A_4$). For example, the monomer from which the repeating units are derived is hydrophobic at about neutral pH. In certain embodiments, the pH-responsive block may become hydrophobic above a pH ranging from 4.0 to 7.0. In some embodiments, the pH-responsive block may become hydrophobic above a pH ranging from 5.0 to about 7.0, or above a pH ranging from about 6.0 to about 7.0, or above a pH ranging from about 5.0 to about 6.5, or above a pH ranging from 5.5 to about 7.0, or above a pH ranging from about 5.5 to about 6.5, or above a pH ranging from about 4.2 to about 6.8, or above a pH ranging from about 4.8 to about 6.0, or above a pH ranging from about 4.8 to about 6.8, or above a pH ranging from about 5.8 to about 6.6, or above a pH ranging from about 4.8 to about 6.4.

In other embodiments, each $A_4$ is a monomer-derived unit with a pKa ranging from about pH 4.2 to about pH 7, or about pH 4.4 to about pH 7, or about pH 4.6 to about pH 7, or about pH 4.8 to about pH 7, or about pH 5 to about pH 7, or about pH 5.2 to about pH 7, or about pH 5.4 to about pH 7, or about pH 5.6 to about pH 7, or about pH 5.8 to about pH 7, or about pH 6 to about pH 7, or about pH 4 to about pH 6.8, or about pH 4 to about pH 6.6, or about pH 4 to about pH 6.6, or about pH 4 to about pH 6.4, or about pH 4 to about pH 6.2, or about pH 4 to about pH 6.

For example, the pH-responsive block may comprise repeating units selected from the group consisting of 2-diisopropylaminoethyl methacrylate, 2-(pentamethyleneimino)ethyl methacrylate, 2-(hexamethyleneimino)ethyl methacrylate, 2-(dipropylamino) ethyl methacrylate, 2-(dibutylamino) ethyl methacrylate, 2-(dipentylamino) ethyl methacrylate and 2-(ethylpropylamino) ethyl methacrylate.

In some embodiments, the hydrophilic polyionic block and the pH-responsive block of the copolymer, independently from each other, may be covalently coupled to a therapeutic cargo such as a nucleic acid or peptide. In certain embodiments, the therapeutic cargo such as a nucleic acid or peptide is covalently linked to the hydrophilic polyionic block or the pH-responsive block through a linker. The linker may be selected from a carbon-carbon bond, an oligonucleotide, a boronate ester bond from by boronic acid and diol, an imine bond, an ester-containing fragment, a thiol-ester, an amide-containing fragment, a disulfide-containing fragment and a 1,2,3-triazole, such as the product of the reaction of an azide and an alkyne ("click chemistry"). In some embodiments, the alkyne coupling partner is part of the hydrophilic polyionic block or the pH-responsive block, and the azide coupling partner is part of the membrane-lytic peptide, therapeutic peptide or nucleic acid. In other embodiments, the azide coupling partner is part of the hydrophilic polyionic block or the pH-responsive block, and the alkyne coupling partner is part of the membrane-lytic peptide, therapeutic peptide or nucleic acid.

Each linker ($L_1$, $L_2$, or $L_3$) may be independently selected in each monomer-derived unit. For example, when o is 2, the copolymer contains two $A_z$ groups, each with a $L_1$ and a $D_1$. The two that can be different or the same. Similarly, the $D_1$ in each $A_1$ monomer-derived unit can be different or the same. The same applies to $L_2$ and $D_2$, as well as $L_3$ and LP.

The targeting group can be a small molecule, an aptamer, a peptide, a protein, an antibody or an antibody fragment.

In some embodiments, $T_1$ and $T_2$ are both absent, while in other embodiments, only one of $T_1$ or $T_2$ is absent. In some embodiments, $T_1$ is a targeting group or therapeutic cargo and $T_2$ is a membrane-lytic entity or therapeutic cargo.

The membrane-lytic entity can be any entity capable of lysing a cell membrane above a critical concentration. In certain embodiments, the membrane-lytic entity is a peptide selected from the group consisting of melittin, peptides from adeno virus protein VI, GALA, KALA, EGLA, JTS1, Gramicidin S, HGP peptide (sequence LLGRRGW-EVLKYWWNLLQYWSQEL), sHGP peptide (sequence RGWEVLKYWWNLLQY), TAT peptide (sequence GRKKRRQRRRPQ), oligoarginine, CaLL (KWKLFK-KIFKRIVQRIKDFLR), hadrurin (GILDTIK-SIASKVWNSKTVQDLKRKGINWVANKLGVSPQAA), cupiennin 1a (GFGALFKFLAKKVAKT-VAKQAAKQGAKYVVNKQME), crabolin (Fmoc-FLAL-ILRKIVTAL-CONH2), IsCT (ILGKIWEGIKSLF-NH2), HsAP (SGTSEKERESGRLLGVVKRLIVCFRSPFP-NH2), Pandinin2 (FWGALAKGALKLIPSLFSSFSKKD), Ponericin (WLGSALKIGAKLLPSVVGLFKKKKQ), UyCT5 (IWSAIWSGIKGLL-NH2) and hemagglutinin.

The therapeutic peptide can be a peptide capable of exerting a biological effect. Examples include peptides for immunostimulation, apoptosis or inhibition of vasoconstriction (e.g. KLA peptide, BH3 peptides, HSP-20 peptide etc).

The nucleic acid can be carry a gene (for example, a plasmid, minicircle, or nanoplasmid), an mRNA, or oligonucleotide (for example, siRNA, DNAzyme, antisense oligonucleotide).

In one embodiment, the block copolymer of Formula (II) has the structure of Formula (IIIa):

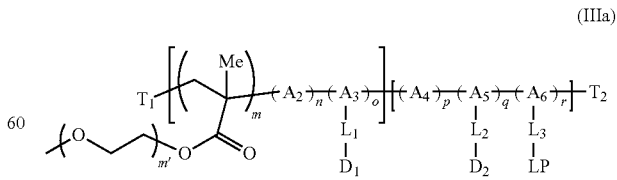

(IIIa)

wherein m' is from about 1 to about 20.

In one embodiment, the block copolymer of Formula (II) has the structure of Formula (IIIb):

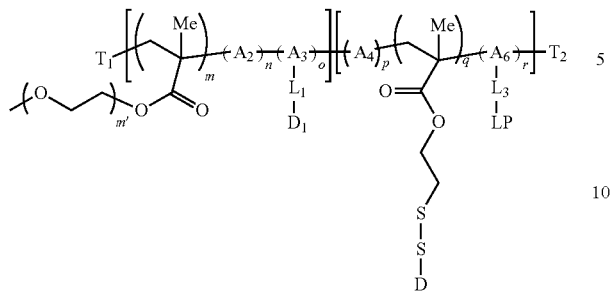
(IIIb)

wherein m' is from about 1 to about 20.

In one embodiment, the block copolymer of Formula (II) has the structure of Formula (IIIc):

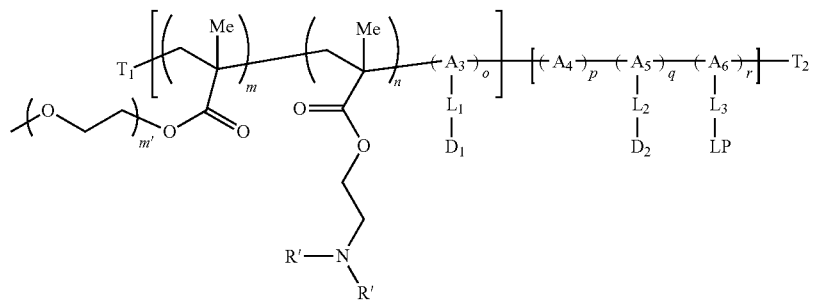
(IIIc)

wherein m' is from about 1 to about 20.

In one embodiment, the block copolymer of Formula (II) has the structure of Formula (IIId):

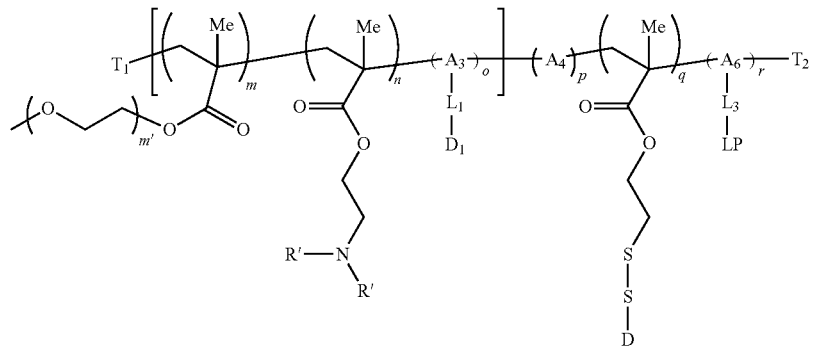
(IIId)

wherein m' is from about 1 to about 20; and each R' is independently hydrogen, alkyl, cycloalkyl, heterocycloalkyl, aryl, alkyl-cycloalkyl, alkyl-heterocycloalkyl or alkyl-aryl.

In one embodiment, the block copolymer of Formula (II) has the structure of Formula (IIIe):

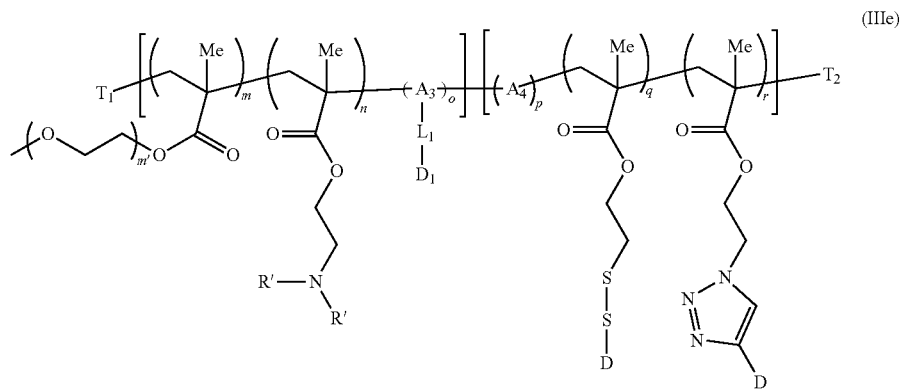

(IIIe)

wherein m' is from about 1 to about 20; and each R' is independently hydrogen, alkyl, cycloalkyl, heterocycloalkyl, aryl, alkyl-cycloalkyl, alkyl-heterocycloalkyl or alkyl-aryl.

In one embodiment, the block copolymer of Formula (II) has the structure of Formula (IIIf):

In one embodiment, the block copolymer of Formula (II) has the structure of Formula (IIIg):

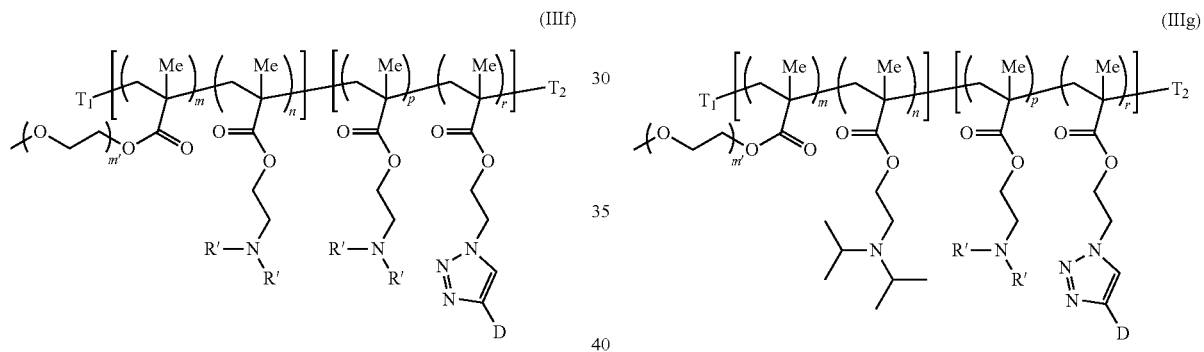

wherein m' is from about 1 to about 20; and each R' is independently hydrogen, alkyl, cycloalkyl, heterocycloalkyl, aryl, alkyl-cycloalkyl, alkyl-heterocycloalkyl or alkyl-aryl.

wherein m' is from about 1 to about 20.

In one embodiment, the block copolymer of Formula (II) has the structure of Formula (IVa):

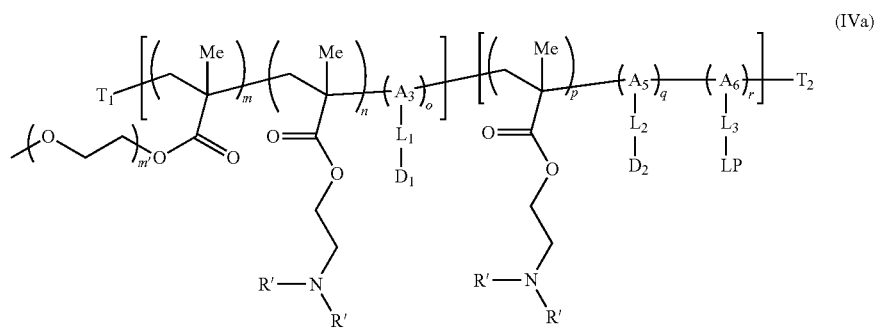

wherein m' is from about 1 to about 20; and each R' is independently hydrogen, alkyl, cycloalkyl, heterocycloalkyl, aryl, alkyl-cycloalkyl, alkyl-heterocycloalkyl or alkyl-aryl.

In one embodiment, the block copolymer of Formula (II) has the structure of Formula (IVb):

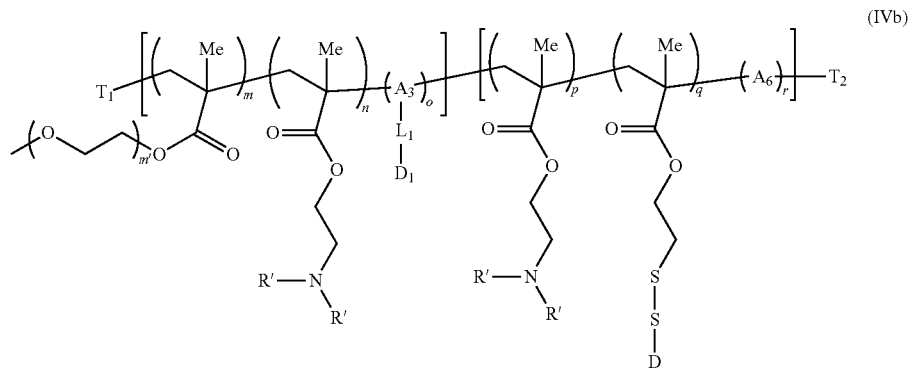

wherein m' is from about 1 to about 20; and each R' is independently hydrogen, alkyl, cycloalkyl, heterocycloalkyl, aryl, alkyl-cycloalkyl, alkyl-heterocycloalkyl or alkyl-aryl.

In one embodiment, the block copolymer of Formula (II) has the structure of Formula (IVc):

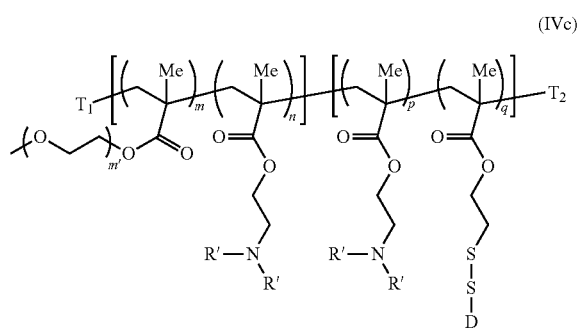

wherein m' is from about 1 to about 20; and each R' is independently hydrogen, alkyl, cycloalkyl, heterocycloalkyl, aryl, alkyl-cycloalkyl, alkyl-heterocycloalkyl or alkyl-aryl.

In one embodiment, the block copolymer of Formula (II) has the structure of Formula (IVd):

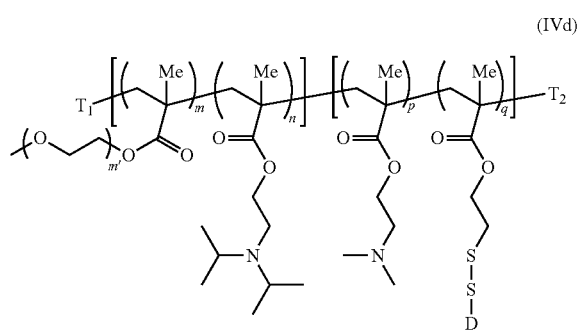

wherein m' is from about 1 to about 20.

In some embodiments, the block copolymer is of Formula (II) where m' is from about 1 to about 20. In some embodiments, is from about 1 to about 15, or about 5 to about 20, or about 5 to 15, or about 10 to about 20, or about 12 to about 20, or about 1 to about 18, or about 5 to about 18.

In some embodiments, the block copolymer is of Formula (II) where each R' is independently hydrogen, alkyl, cycloalkyl, heterocycloalkyl or aryl. In other embodiments, each R' is independently hydrogen, alky alkyyl-cycloalkyl, alkyl-heterocycloalkyl or alkyl-aryl. In other embodiments, each R' is independently hydrogen, alkyl, cycloalkyl, aryl, alkyl-cycloalkyl or alkyl-aryl. In other embodiments, each R' is independently hydrogen or alkyl. In some embodiments, each R' is independently hydrogen, methyl, ethyl, n-propyl, iso-propyl, n-butyl, iso-butyl, tert-butyl, n-pentyl, iso-pentyl or hexyl. In some embodiments, each R' is independently methyl, ethyl, n-propyl, iso-propyl, n-butyl, iso-butyl, tert-butyl, n-pentyl, iso-pentyl or hexyl.

In some embodiments, the block copolymer is of Formula (II) where m is from about 1 to about 10,000;
n is from about 1 to about 10,000;
o is from about 0 to about 10,000;
p is from about 1 to about 10,000;
q is from about 0 to about 10,000; and
r is from about 0 to about 10,000.

In some embodiments, the block copolymer is of Formula (II) where
m is from about 1 to about 10,000;
n is from about 0 to about 10,000;
o is from about 0 to about 10,000;
p is from about 1 to about 10,000;
q is from about 0 to about 10,000; and
r is from about 0 to about 10,000.

In some embodiments, the block copolymer is of Formula (II) where
m is from about 1 to about 10,000;
n is from about 0 to about 10,000;
o is from about 0 to about 10,000;
p is from about 1 to about 10,000;
q is from about 0 to about 10,000; and
r is from about 1 to about 10,000.

In some embodiments, the block copolymer is of Formula (II) where
m is from about 1 to about 10,000;
n is from about 1 to about 10,000;
o is from about 0 to about 10,000;

p is from about 1 to about 10,000;
q is from about 0 to about 10,000; and
r is from about 0 to about 10,000.

In some embodiments, the block copolymer is of Formula (II) where
m is from about 1 to about 10,000;
n is from about 1 to about 10,000;
o is from about 0 to about 10,000;
p is from about 1 to about 10,000;
q is from about 0 to about 10,000; and
r is from about 1 to about 10,000.

In some embodiments, the block copolymer is of Formula (II) where
m is from about 1 to about 10,000;
n is from about 0 to about 10,000;
o is from about 1 to about 10,000;
p is from about 1 to about 10,000;
q is from about 1 to about 10,000; and
r is from about 0 to about 10,000.

In some embodiments, the block copolymer is of Formula (II) where
m is from about 1 to about 10,000;
n is from about 0 to about 10,000;
o is from about 0 to about 10,000;
p is from about 1 to about 10,000;
q is from about 0 to about 10,000; and
r is from about 1 to about 10,000.

In some embodiments, the block copolymer is of Formula (II) where
m is from about 1 to about 10,000;
n is from about 1 to about 10,000;
o is from about 1 to about 10,000;
p is from about 1 to about 10,000;
q is from about 1 to about 10,000; and
r is from about 0 to about 10,000.

In some embodiments, the block copolymer is of Formula (II) where
m is from about 1 to about 10,000;
n is from about 1 to about 10,000;
o is from about 0 to about 10,000;
p is from about 1 to about 10,000;
q is from about 0 to about 10,000; and
r is from about 1 to about 10,000.

In some embodiments, the block copolymer is of Formula (II) where
m is from about 1 to about 10,000;
n is from about 0 to about 10,000;
o is from about 1 to about 10,000;
p is from about 1 to about 10,000;
q is from about 1 to about 10,000; and
r is from about 0 to about 10,000.

In some embodiments, the block copolymer is of Formula (II) where
m is from about 1 to about 10,000;
n is from about 0 to about 10,000;
o is from about 0 to about 10,000;
p is from about 1 to about 10,000;
q is from about 0 to about 10,000; and
r is from about 1 to about 10,000.

In some embodiments, the block copolymer is of Formula (II) where
m is from about 1 to about 10,000;
n is from about 1 to about 10,000;
o is from about 1 to about 10,000;
p is from about 1 to about 10,000;
q is from about 1 to about 10,000; and
r is from about 0 to about 10,000.

In some embodiments, the block copolymer is of Formula (II) where
m is from about 1 to about 10,000;
n is from about 1 to about 10,000;
o is from about 1 to about 10,000;
p is from about 1 to about 10,000;
q is from about 0 to about 10,000; and
r is from about 1 to about 10,000.

In some embodiments, the block copolymer is of Formula (II) where
m is from about 1 to about 10,000;
n is from about 1 to about 10,000;
o is from about 0 to about 10,000;
p is from about 1 to about 10,000;
q is from about 0 to about 10,000; and
r is from about 1 to about 10,000.

In some embodiments, the block copolymer is of Formula (II) where
m is from about 1 to about 10,000;
n is from about 0 to about 10,000;
o is from about 1 to about 10,000;
p is from about 1 to about 10,000;
q is from about 0 to about 10,000; and
r is from about 1 to about 10,000.

In some embodiments, if r is 0 then $T_2$ is a membrane-lytic peptide, a therapeutic peptide, a nucleic acid or nucleic acid derivative (i.e., not absent). In another embodiment, if r is 0 then a membrane-lytic peptide, a therapeutic peptide, a nucleic acid or nucleic acid derivative can be incorporated into the pH-responsive block (i.e., $A_4$, $A_5$ or $A_6$).

In the second aspect, the present invention provides a method for providing a copolymer according to any of the copolymers described further herein. The method includes combining monomers corresponding to the monomer-derived units of the copolymer and initiating polymerization. The polymerization conditions can be selected from any known in the art to polymerize the monomers to provide the copolymer of the invention. In some embodiments, the polymerization is performed under RAFT conditions.

In a third aspect, the present invention provides micellar assembly comprising: a plurality of copolymers according to any of the copolymers described herein. In certain embodiments, the micellar assembly has a diameter of about 5 nm to about 100 nm. In certain embodiments, the micellar assembly disassembles of pH of less than about 6.5.

In a fourth embodiment, the present invention provides a pharmaceutical composition comprising at least one of at least one of a block copolymer according to any aspect of this invention and a micellar assembly according aspect of this invention; and a therapeutic agent reversibly associated with the hydrophilic polyionic block. In certain embodiments, the therapeutic agent is a nucleic acid molecule. In certain embodiments, the therapeutic agent is a protein or peptide.

In a fifth aspect, the present invention provides a method of intracellularly delivering a therapeutic agent comprising: administering the pharmaceutical composition described herein to a subject, wherein the pharmaceutical composition is endocytosed into the endosome and the pharmaceutical composition, thereby, releases the therapeutic agent into the endosome. The therapeutic agent can be a substance capable of producing a therapeutic effect for the treatment of a disease or condition. In some embodiments, the therapeutic agent is a nucleic acid. In some embodiments, the administration is intravenous, intratrachael, intraventricular or intratumoral subcutaneous.

EXAMPLES

A self-assembling synthetic polymer containing a hidden membrane-lytic peptide at neutral pH was designed. This polymer undergoes a conformational change in acidic environments such as the early endosome to unveil the peptide for selective endosomal membrane disruption. The peptide employed is melittin that can insert into lipid membranes and induce pore formation. M. T. Tosteson et al. *Biophysical Journal,* 36, 109-116. Melittin has been conjugated to various cationic polymers and shown to enhance gene transfer ability by promoting endosomal release of vectors. M. Ogris et al. *Journal of Biological Chemistry* 2001, 276, 47550-47555.

It is demonstrated that the melittin-containing polymer, VIPER, has selective membrane-lytic ability at acidic pH. VIPER effectively packages plasmid DNA for delivery into a variety of mammalian cells with efficiencies higher than commercial agents. Finally, it is show that VIPER can be used for efficient in vivo gene transfer into tumors, overcoming the in vitro/in vivo disconnects observed for many polycation gene delivery systems.

Figure 4:
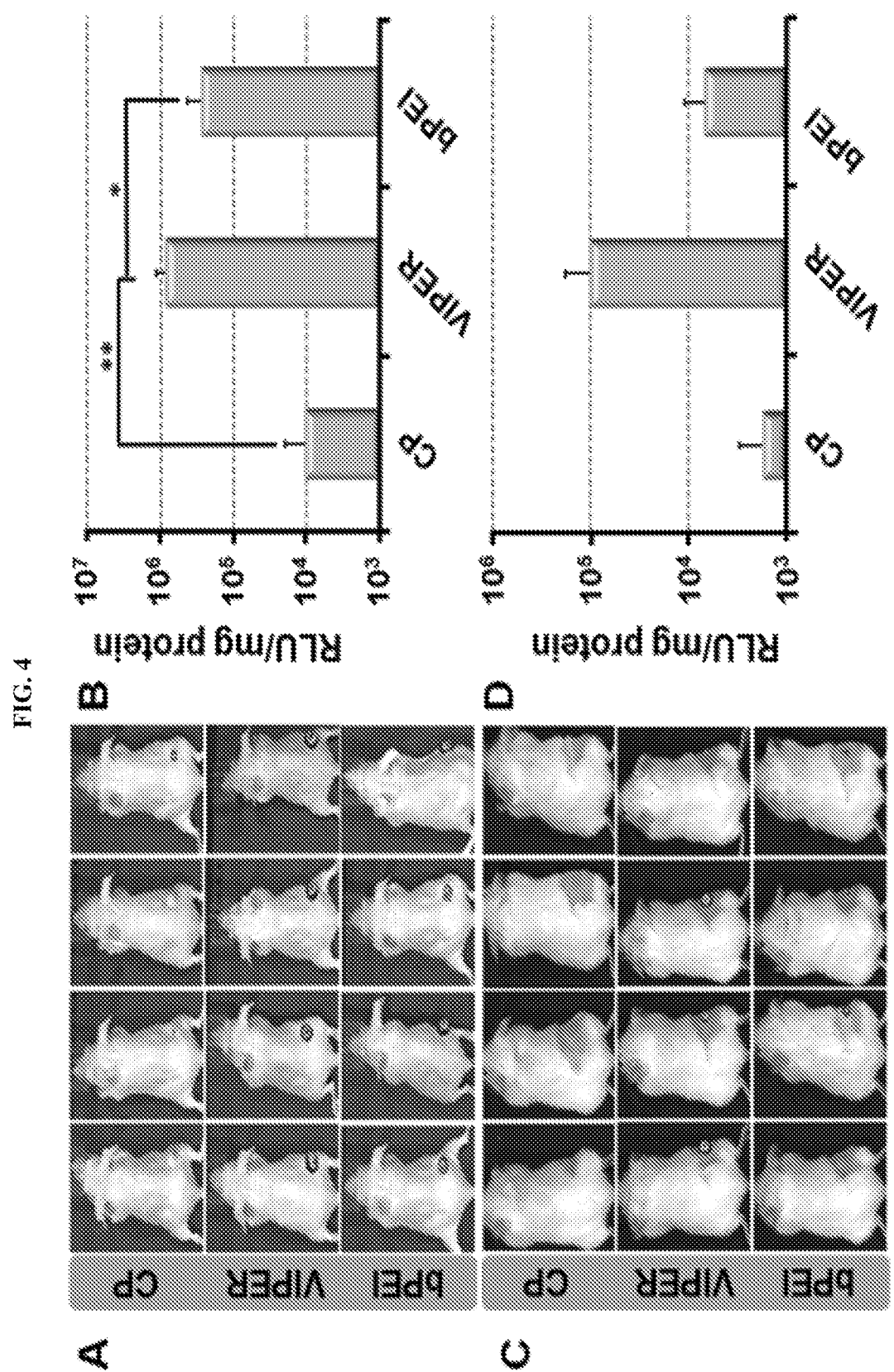
FIG. 4 shows A). Bioluminescence images of KB tumor-bearing mice treated by intratumoral injection with various polyplexes. B). Luciferase activity from excised KB tumor tissues of mice treated with polyplexes. C). Bioluminescence images of A549 tumor-bearing mice treated by intratumoral injection with various polyplexes. D). Luciferase activity from excised A549 tumor tissues of mice treated with polyplexes. Data are shown as mean±SD (n=4; student's t test, *p<0.05. p<0.01, *p<0.001).
Figure 5:
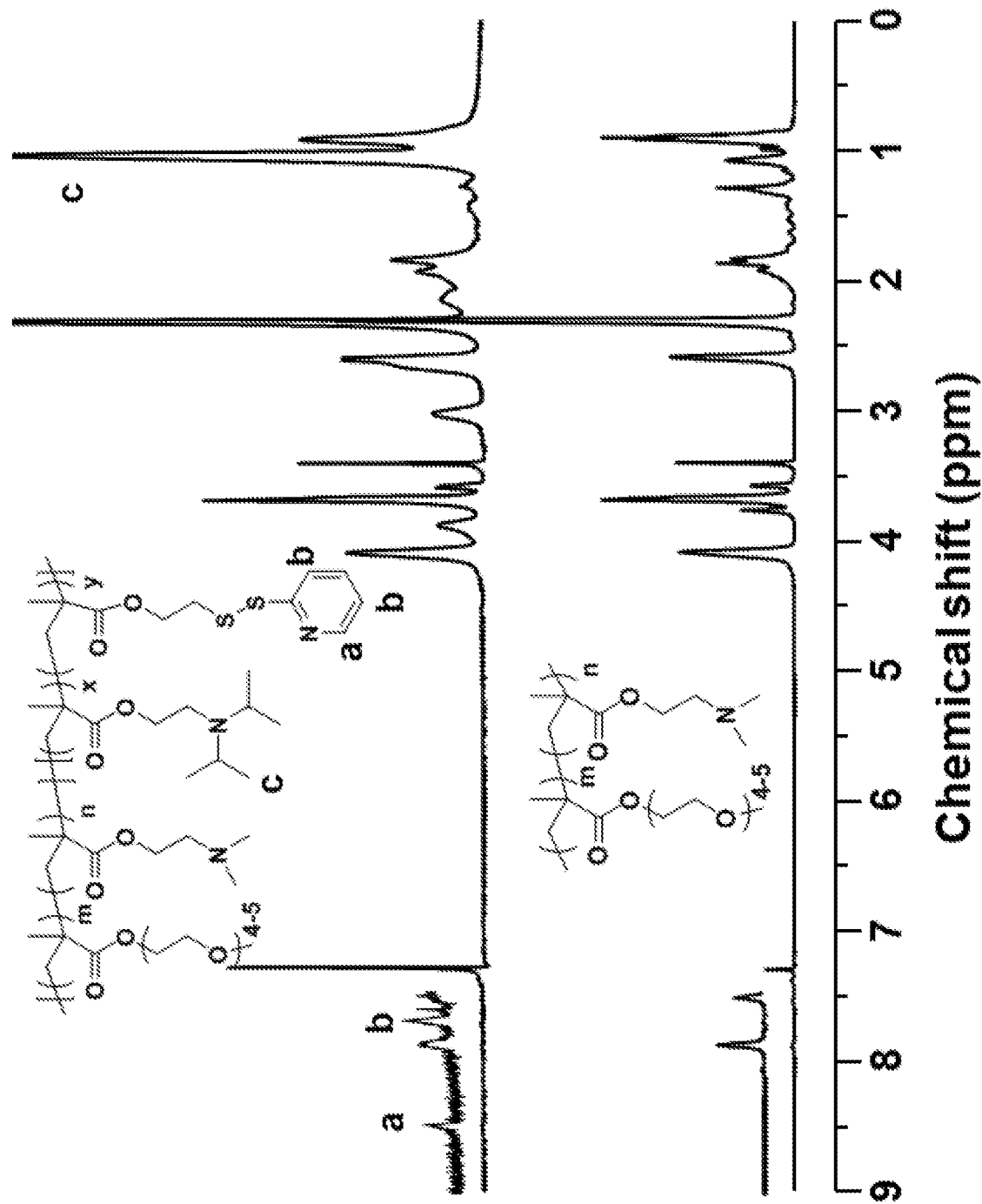
FIG. 5 shows a $^1$H NMR spectra of p(OEGMA$_{11}$-DMAEMA$_{56}$) and p(OEGMA$_{11}$-DMAEMA$_{56}$)-b-p(DIPAMA$_{33}$-PDSEMA$_1$).

Reversible addition-fragmentation chain transfer (RAFT) polymerization (see D. S. H. Chu et al. *Accounts Chem Res* 2012, 45, 1089-1099) was used to synthesize VIPER, which is composed of a hydrophilic cationic block for nucleic acid loading and a pH-sensitive block for triggered display of a membrane-lytic peptide (FIG. 1A). The hydrophilic cationic block, poly(oligo(ethylene glycol) monomethyl ether methacrylate)-co-poly(2-(dimethylamino)ethyl methacrylate) (p(OEGMA-DMAEMA)), includes DMAEMA, widely used in polycations for nucleic acid delivery, and OEGMA, a hydrophilic monomer to provide colloidal stability. P. van de Wetering et al. *J Control Release* 1998, 53, 145-153; b) H. Wei et al. *Angew Chem Int Edit* 2013, 52, 5377-5381. The pH-sensitive block, poly(2-diisopropylaminoethyl methacrylate)-co-poly(pyridyl disulfide ethyl methacrylate) (p(DIPAMA-PDSEMA)), includes p(DIPAMA)), a pH sensitive polymer which features a sharp phase transition from hydrophobic to hydrophilic at pH 6.3, (Y. G. Wang et al. *Nat Mater* 2014, 13, 204-212) and PDSEMA monomers to enable further functionalization with thiol-containing peptides through disulfide exchange reaction. The successful synthesis of the copolymer, p(OEGMA11-DMAEMA56)-b-p(DIPAMA33-PDSEMA1) (control polymer used for further studies, denoted as CP), and VIPER (CP grafted with melittin) were characterized by 1H NMR (FIG. 4), GPC and UV spectroscopy (FIG. 5).

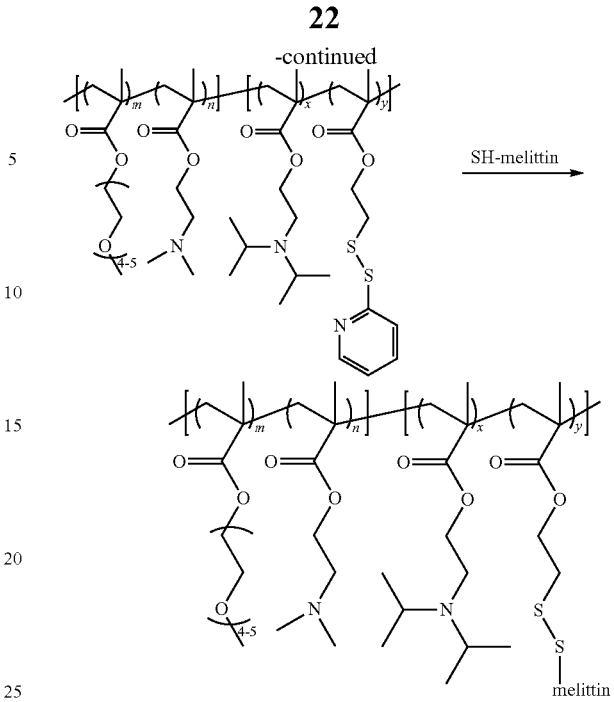

VIPER was therefore designed to self-assemble into micellar structures at physiological pH with melittin buried within the hydrophobic core. After endocytosis, the acidic endosomal environment triggers a hydrophilic transition of the pDIPAMA block, unveiling the melittin peptide, which can then facilitate endosomal release by disruption of the endo/lysosome membrane (FIG. 1B).

Figure 2:
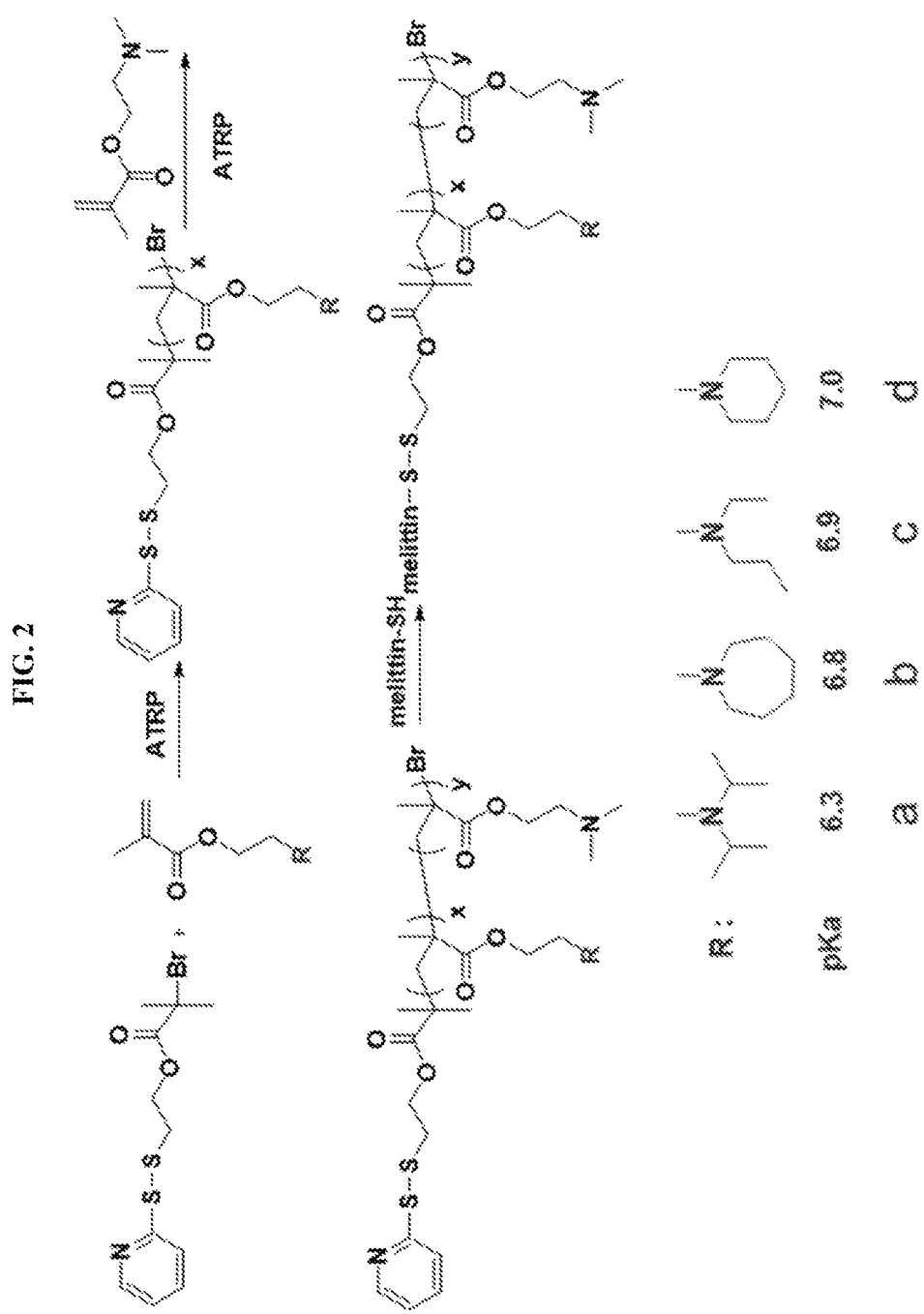
FIG. 2 shows the chemical structure of alternative embodiments of VIPER that undergo the hydrophobic to hydrophilic transition at various acidic pHs.

To verify this hypothesized mechanism, the assembly behavior of VIPER at pH 7.4 and pH 5.7 was monitored by both transmission electron microscopy (TEM) imaging and dynamic light scattering (DLS) analysis. VIPER assembles into uniform spherical nanoparticles with diameter around 30 nm at pH 7.4 (FIGS. 2A and C for TEM and DLS, respectively). However, at pH 5.7, no assemblies were observed by either method, suggesting complete dissociation of nanoparticles at endosomal pH (FIGS. 2B and C). This data validates the pH-triggered phase transition of VIPER.

Next, a hemolysis study was conducted to evaluate the acid-triggered display of melittin. At pH 7.4, no significant cell lysis was observed even at VIPER concentrations as high as 240 μg/mL after incubation with human red blood cells, confirming encapsulation and masking of melittin within the hydrophobic domain of the nanoparticles (FIG. 2D). At pH 5.7, cell lysis was observed with a concentration dependent profile; 50% lysis was achieved with only 30 μg/mL VIPER and complete lysis occurred with 120 μg/mL VIPER. Meanwhile, no significant membrane lysis was observed for CP in all testing conditions, indicating that membrane lysis is caused by the melittin rather than polymer backbone.

Figure 6:
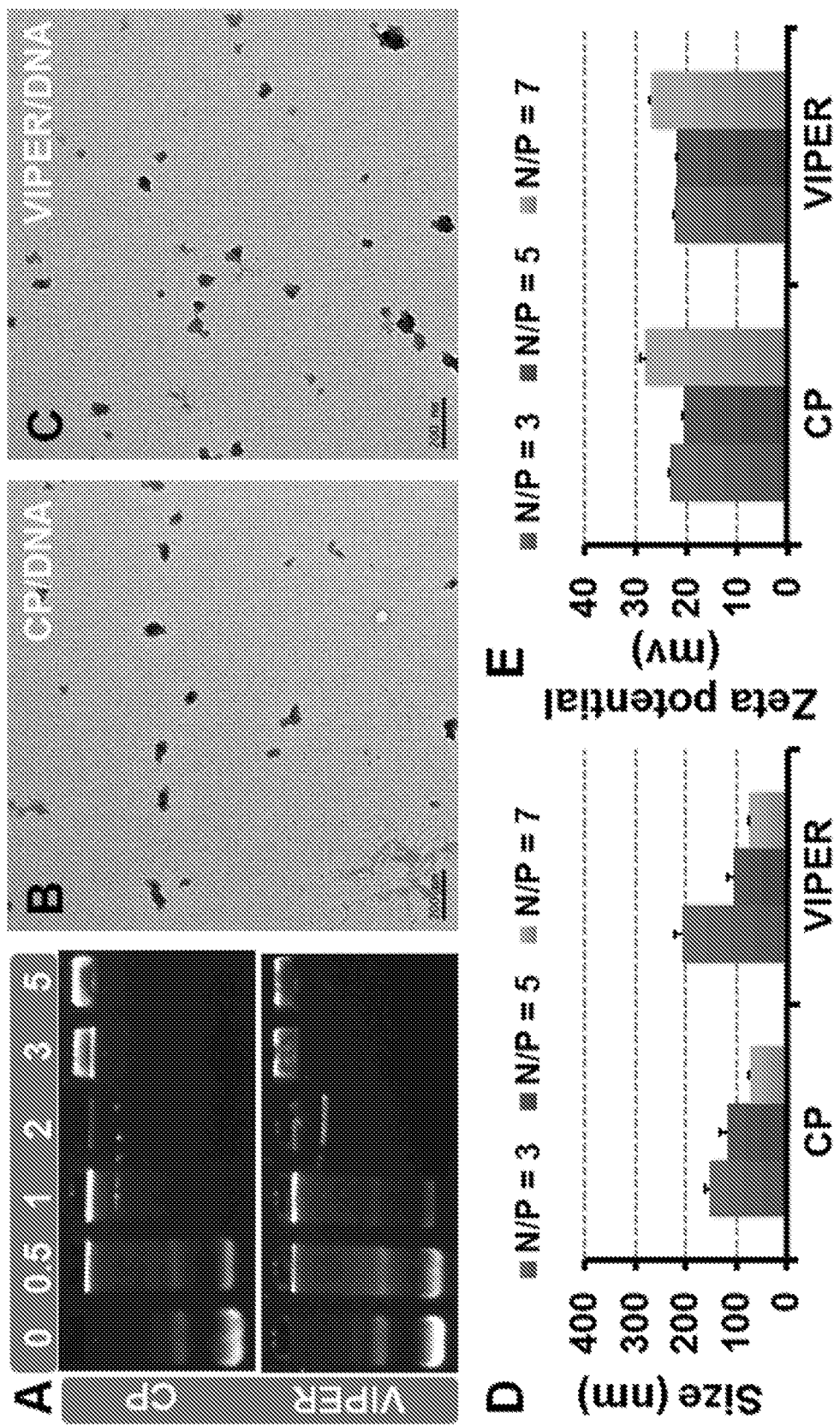
FIG. 6 shows the characterization of the polymer/DNA polyplexes. A). Agarose gel electrophoresis of polymer/DNA complexes prepared at different N/P ratios. B) and C). TEM images of polymer/DNA complexes formed at N/P=5 (scale bar: 200 nm). D). Average hydrodynamic diameters of different formulations. E). Zeta potential of different formulations. Data are shown as mean±SD (n=3).
Figure 7:
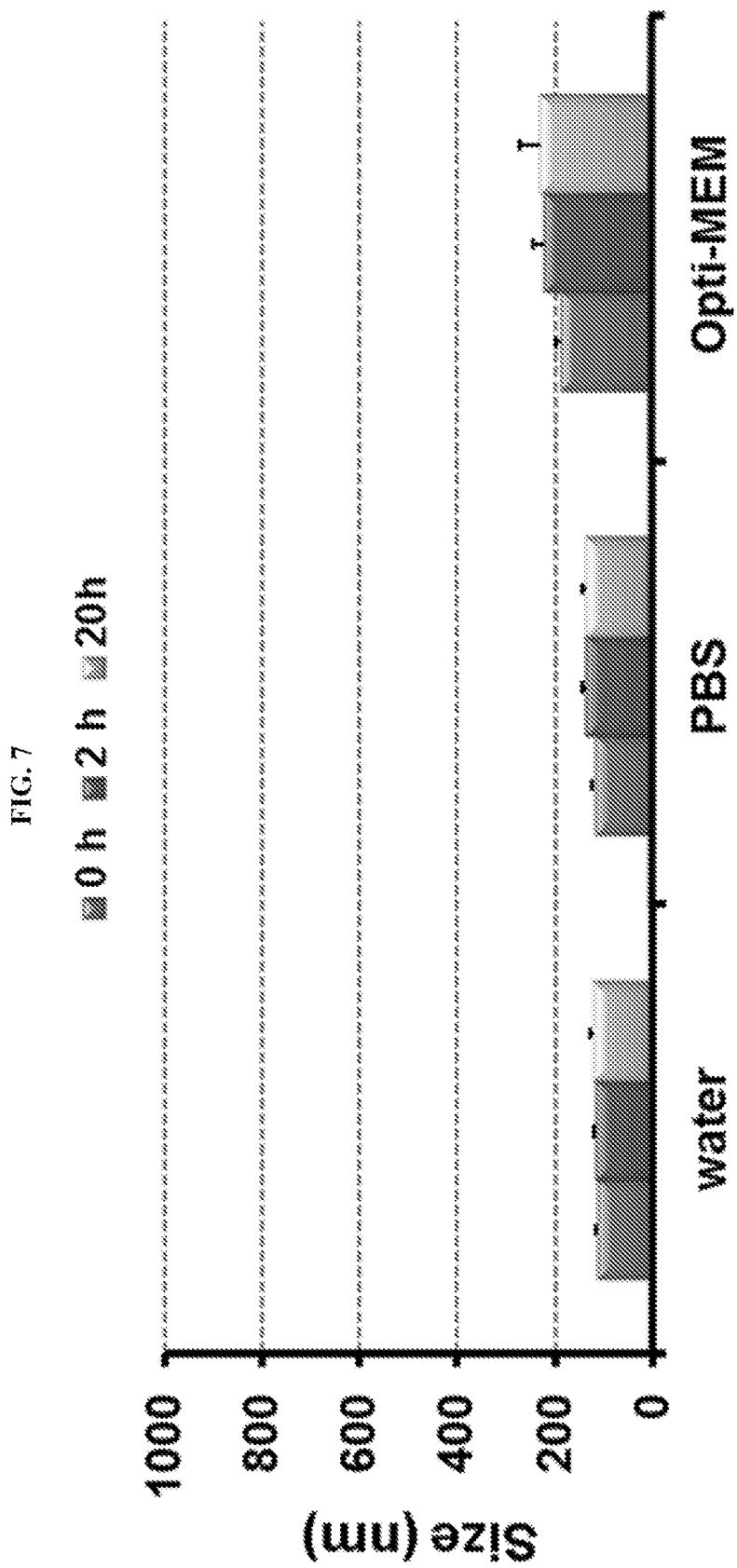
FIG. 7 shows the stability testing of polyplexes formed by DNA and VIPER (N/P=5) under different conditions. Data are shown as mean±SD (n=3).

The polymers were then complexed with plasmid DNA to form polyplexes for gene delivery. VIPER and CP efficiently packaged plasmid DNA, with complete condensation at N/P (amine to phosphate) ratios of 2. TEM imaging of VIPER and CP polyplexes (N/P=5) revealed compact structures with relatively uniform spherical shape and diameters <100 nm (FIGS. 6B and C). DLS measurements of size were consistent with TEM images, and showed that particle sizes were similar between VIPER and CP complexes, and decreased with increasing N/P ratio (FIGS. 6D, 7). When formulated at N/P≥3, surface charge of both VIPER and CP complexes were positive. Finally, a hemolysis study with CP/DNA and VIPER/DNA polyplexes confirmed that pH-sensitive membrane lysis was retained in the polyplex formulation (FIG. 7). Cell lysis was observed with VIPER/DNA polyplexes at pH.5.7 but minimally at pH 74 and CP/DNA polyplexes were not membrane active at either pH.

Figure 8:
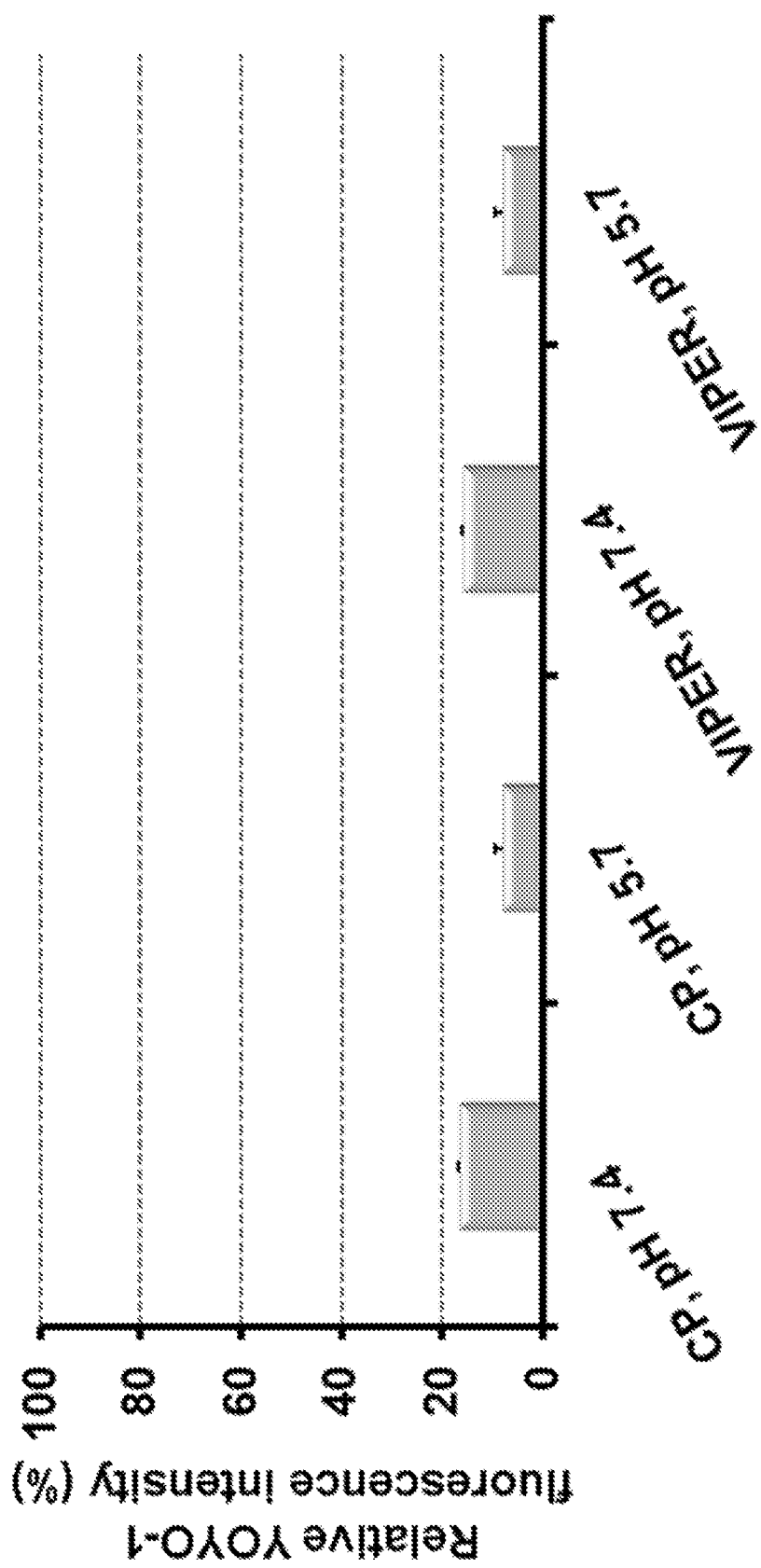
FIG. 8 shows hemolysis activity of CP/DNA and VIPER/DNA polyplexes at various polymer concentrations and pHs. The N/P ratio used in the formulations was 7. Data are shown as mean±SD (n=3).

The lytic peptide melittin in VIPER is expected to induce the endo/lysosome escape of polyplexes. To evaluate endosomal release, both YOYO-1 labeled VIPER and CP polyplexes delivery to HeLa cells was tracked by triple fluorescence confocal microscopy after confirming that YOYO-1 fluorescence in polyplexes can be detected at both acidic and neutral pH (FIG. 8). After 4 h incubation, most of the green fluorescence (YOYO-1 DNA) from VIPER polyplexes was separated from the red fluorescence (LysoTracker Red), indicating efficient endo/lysosomal escape of VIPER/DNA polyplexes. Conversely, nearly complete colocalization (yellow) of green and red fluorescence was observed in cells treated with CP polyplexes. The colocalization ratio of VIPER polyplexes with lysosomes was only 9.4%, compared with CP polyplexes (72.2%). Our previous work showed that bPEI polyplexes show similar intracellular distribution profiles as CP polyplexes, indicating endosomal trapping. E. J. Kwon, J. M. Bergen, S. H. Pun, *Bioconjugate Chemistry* 2008, 19, 920-927. It is worthwhile to mention that there is no significant difference observed in cellular uptake efficiency between CPiDNA and VIPER/DNA complexes as determined by flow cytometry (FIG. 8). Thus, VIPER polyplexes offer significantly improved endosomal release of nucleic acid cargo within mammalian cells compared to CP.

Figure 9:
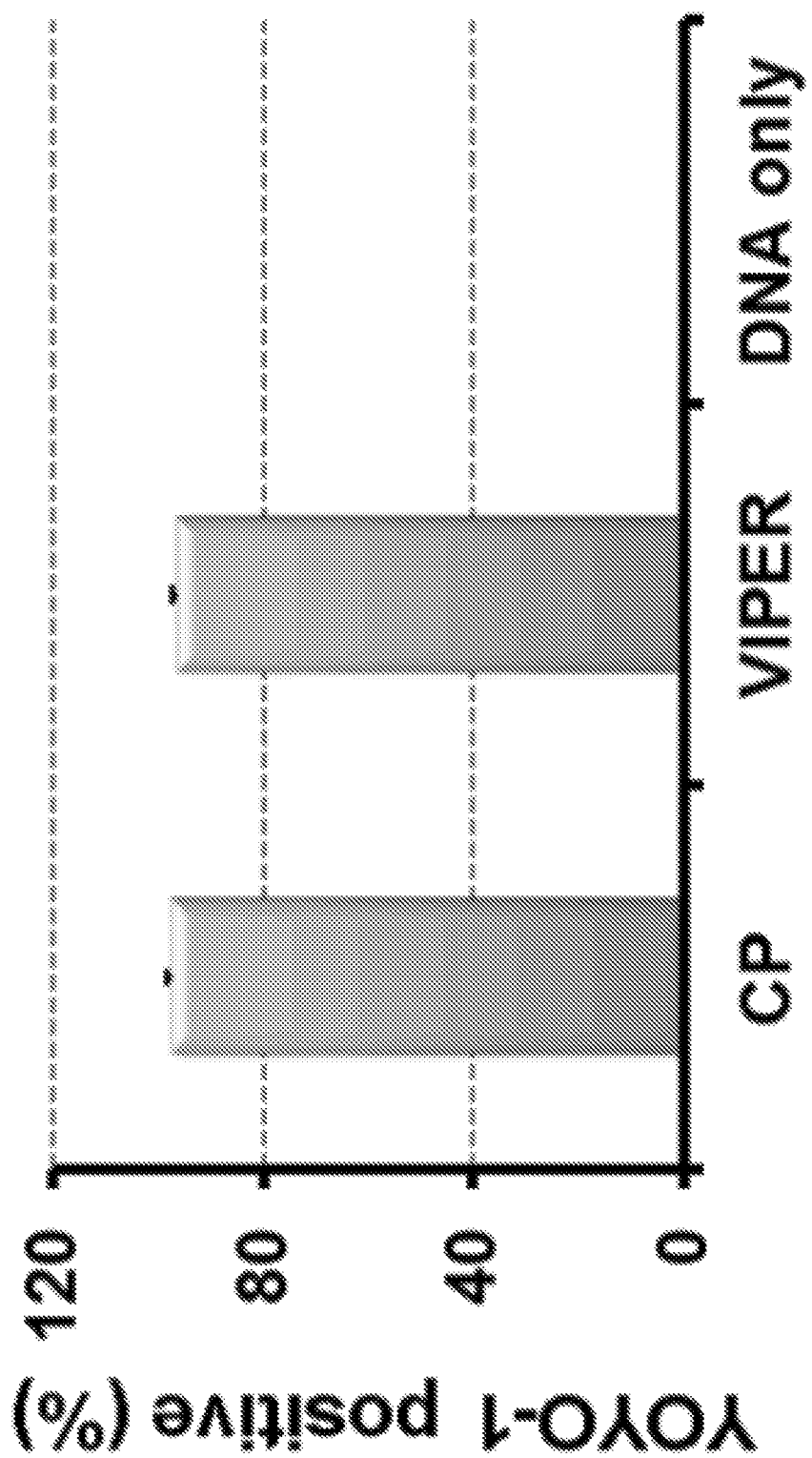
FIG. 9 shows the cellular uptake of polyplexes formed by CP and VIPER with DNA (N/P=5). DNA was labeled with YOYO-1. Data are shown as mean±SD (n=3).
Figure 10:
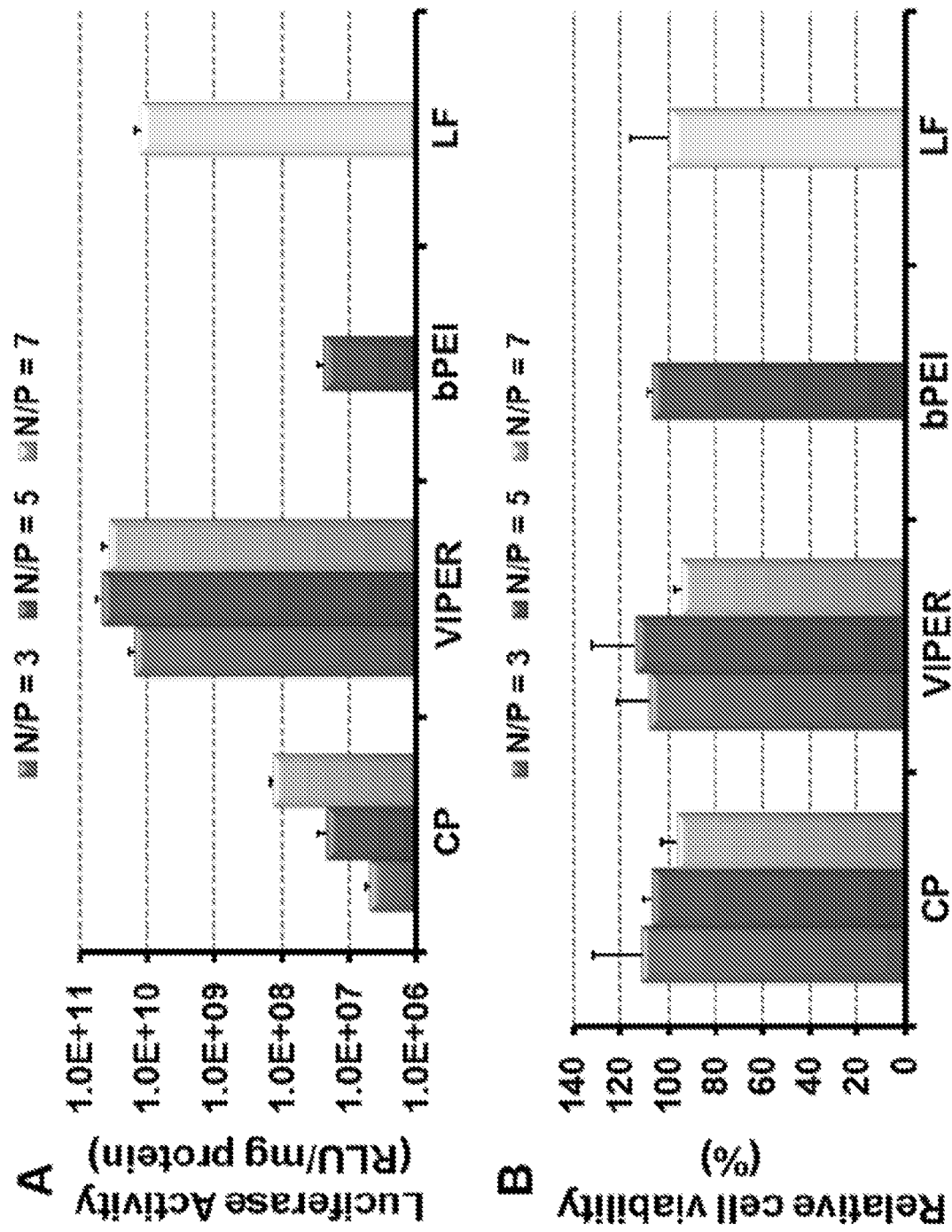
FIG. 10. In vitro transfection with HeLa cells with various polyplexes at different N/P ratios. A). Transfection efficiency. B). Relative cell viability. Data are shown as mean±SD (n=3).
Figure 11:
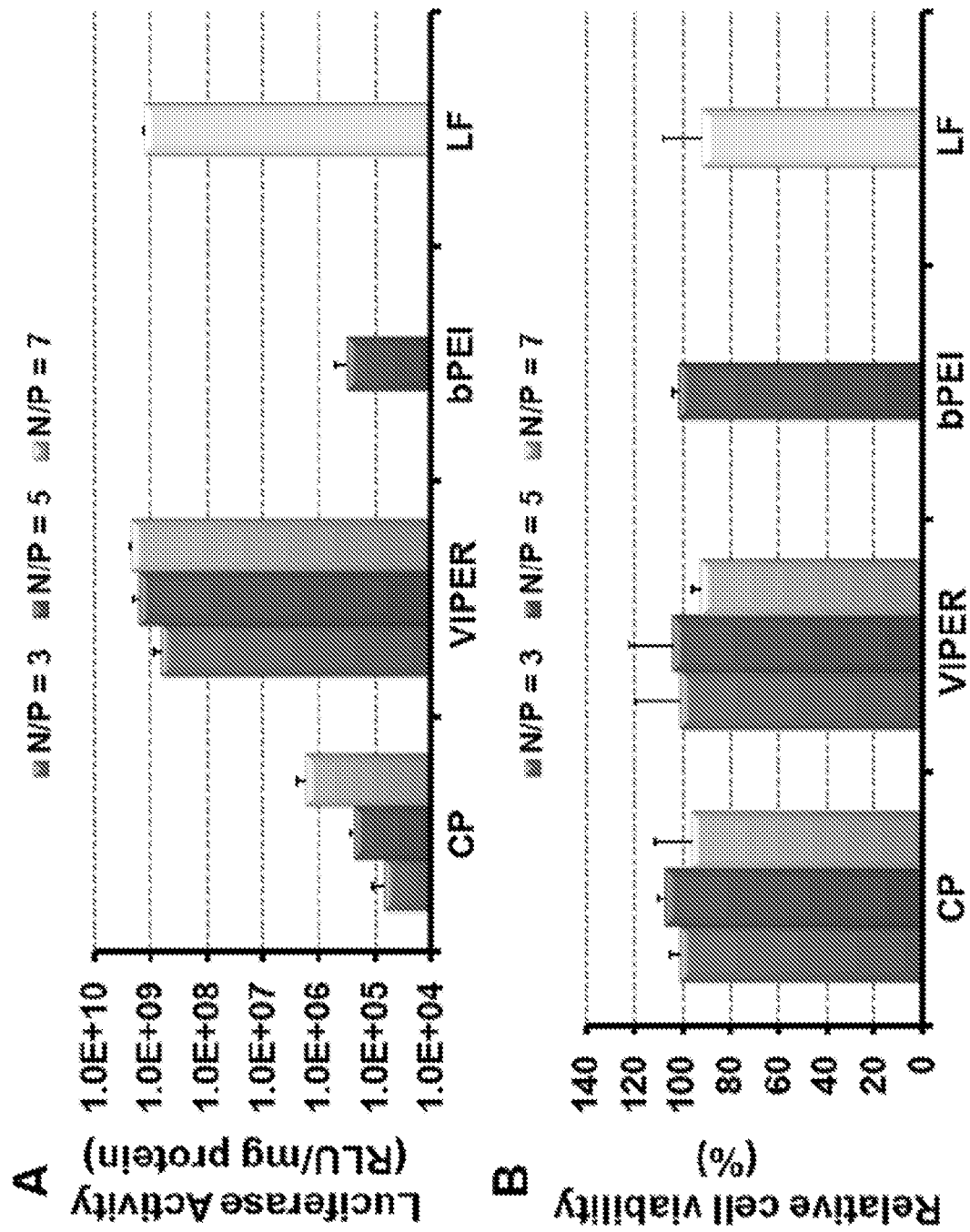
FIG. 11 shows the in vitro transfection with KB cells with various polyplexes at different N/P ratios. A). Transfection efficiency. B). Relative cell viability. Data are shown as mean±SD (n=3).
Figure 12:
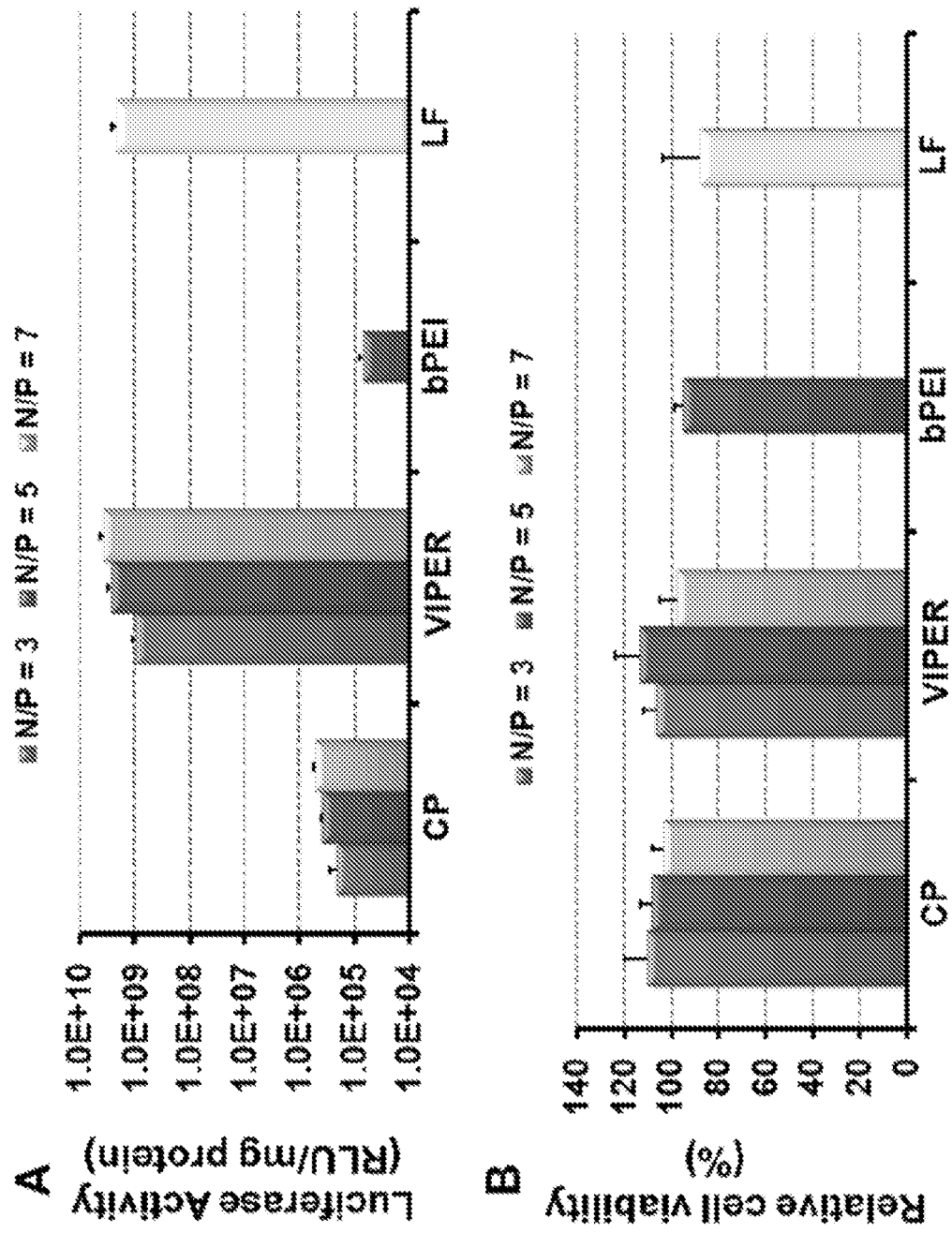
FIG. 12 shows the in vitro transfection with Z310 cells with various polyplexes at different N/P ratios. A). Transfection efficiency. B). Relative cell viability. Data are shown as mean±SD (n=3).
Figure 13:
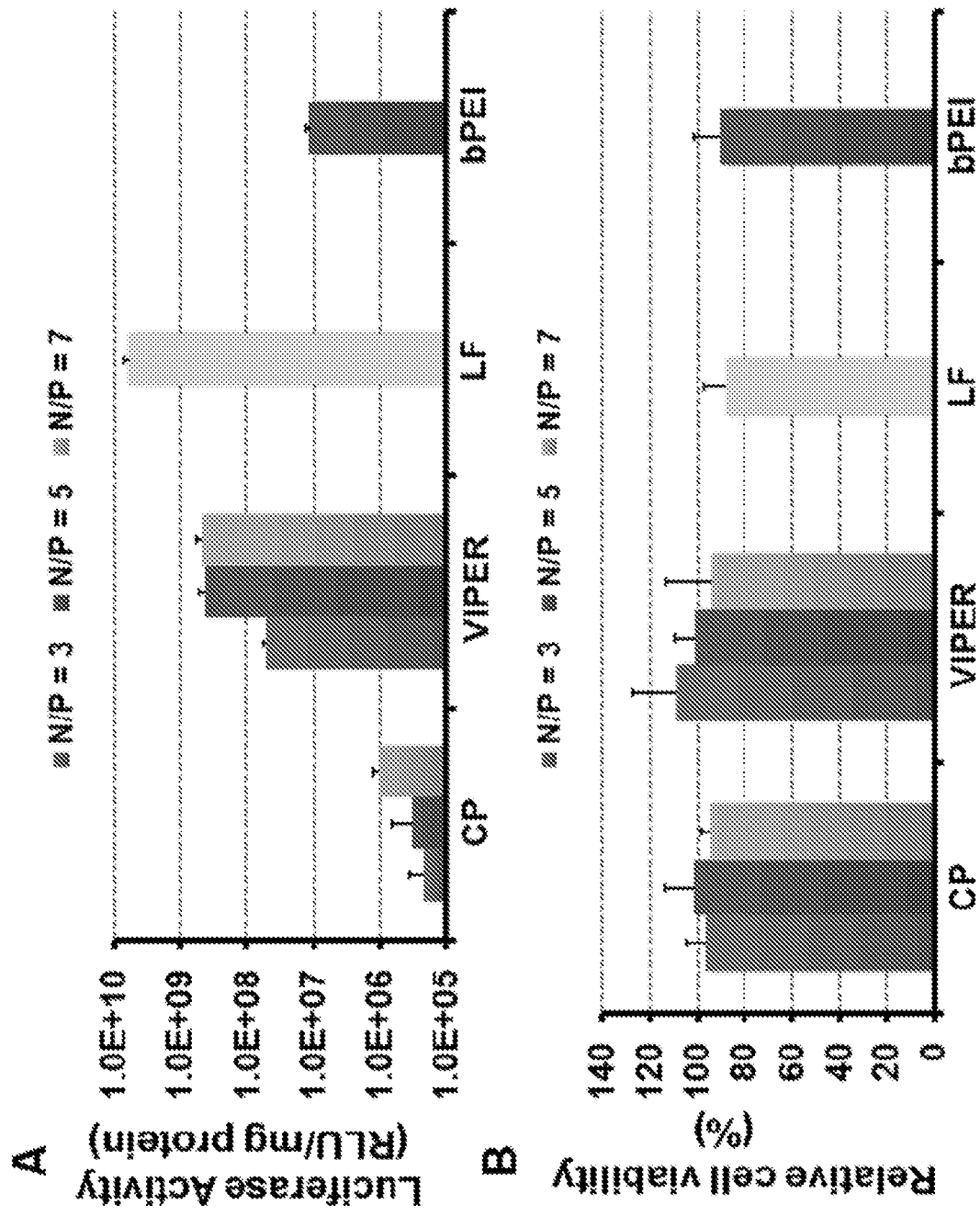
FIG. 13 shows the in vitro transfection with A549 cells with various polyplexes at different N/P ratios. A). Transfection efficiency. B). Relative cell viability. Data are shown as mean±SD (n=3).
Figure 14:
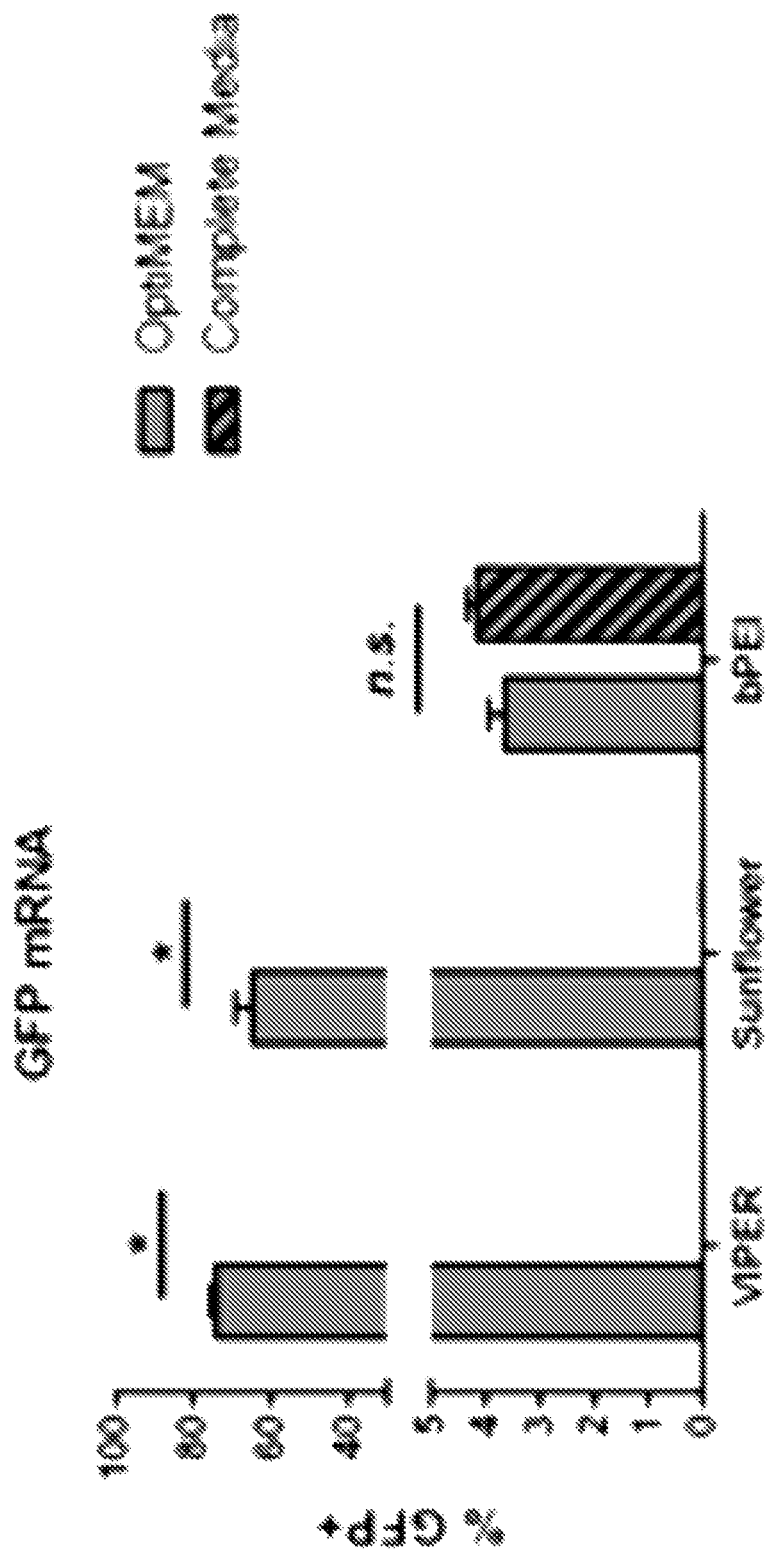
FIG. 14 shows the in vitro transfection of HeLa cells with polyplexes formed by electrostatic complexation of VIPER, a cationic pDMAEMA sunflower polymer, and branched polyethylenimine (bPEI) for messenger (mRNA) delivery.

Next, the in vitro gene delivery efficiency of CP and VIPER polyplexes was tested in a panel of immortalized mammalian cell lines (HeLa and KB cervical carcinoma, A549 lung carcinoma and Z310 choroidal epithelial cells) using the reporter luciferase plasmid. The polycation standard, branched PEI (bPEI, 25 kDa) and commercial transfection reagent, lipofectamine 2000 (LF), were used for comparison. The luciferase activity obtained by VIPER transfection was orders of magnitude higher than that by CP and bPEI in all tested cell lines (FIG. 9). VIPER also mediated improved transfection efficiency compared to optimized LF formulations in HeLa, KB and Z310 cells. VIPER polyplexes were well-tolerated; cell viability remained >90% in all cell types at all tested N/P ratios (FIG. 9). The transfection experiment was then repeated using reporter plasmid carrying the green fluorescent protein gene (GFP) to determine the percent of transfected cells. The same transfection trend as the luciferase experiment was observed for all the cell lines. VIPER transfected 13- to 60-fold more cells compared to CP and 11- to 46-fold more cells compared to bPEI, with efficiencies ranging from 36-77% GFP+ cells.

Gene therapy is being recognized as a potent method to treat various malignant tumors, and several polycation-based gene vectors have entered into different clinical phases. H. Yin, R. L. Kanasty, A. A. Eltoukhy, A. J. Vegas, J. R. Dorkin, D. G. Anderson, *Nat Rev Genet* 2014, 15, 541-555. In order to investigate the potential of VIPER as gene vectors to treat cancers, in vivo gene transfer by direct delivery of luciferase plasmid containing polyplexes to solid tumors in both KB and A549 xenograft tumor models were evaluated. VIPER and bPEI polyplexes, which have membrane-lytic peptide (VIPER) and proton sponge (bPEI) mechanisms of endosomal escape, efficiently delivered plasmid to KB tumors in contrast to CP, confirming by their intensive bioluminescence in tumor sites (FIG. 3A). Tumors treated with VIPER polyplexes showed the highest luciferase activity, 3.1- and 82.5-fold higher than bPEI and CP polyplexes treated groups, respectively (FIG. 3B). VIPER polyplexes also outperformed both bPEI and CP polyplexes in intratumoral gene transfer to A549 xenograft tumors by 15.1-fold and 59.7-fold, respectively (FIGS. 3C and D). These results confirm that VIPER can efficiently mediate both in vitro and in vivo gene transfer to dividing cells.

Trapping within endo/lysosomal vehicles is a major barrier in delivery of most macromolecular drugs with intracellular targets. For gene transfer, lysosomal nucleases such as DNase II degrade nucleic acids, compromising gene transfer efficiency. D. Pinto-Gonzalez Howell et al. *Mol Ther* 2003, 8, 957-963. To address this issue, diverse systems have been exploited, such as proton sponge effect and the employment of synthetic or virus-derived membrane-active peptides. However, some previous work has revealed that the "proton sponge effect" alone is not sufficient for endo/lysosomal escape. Y. Y. Won et al. *J Control Release* 2009, 139, 88-93. Although the direct conjugation of lytic peptide with polycation carriers improves transfection efficiency, significant cytotoxicity is typically associated with the peptides. For example, our previous work showed that the incorporation of either melittin or sHGP peptides to polycations results in cytotoxicity due to the exposure of lytic peptide in physiological conditions and the destabilization of the plasma membrane. E. J. Kwon et al. *Molecular Pharmaceutics* 2010, 7, 1260-1265; J. G. Schellinger et al. *Biomaterials* 2013, 34, 2318-2326.

Figure 3:
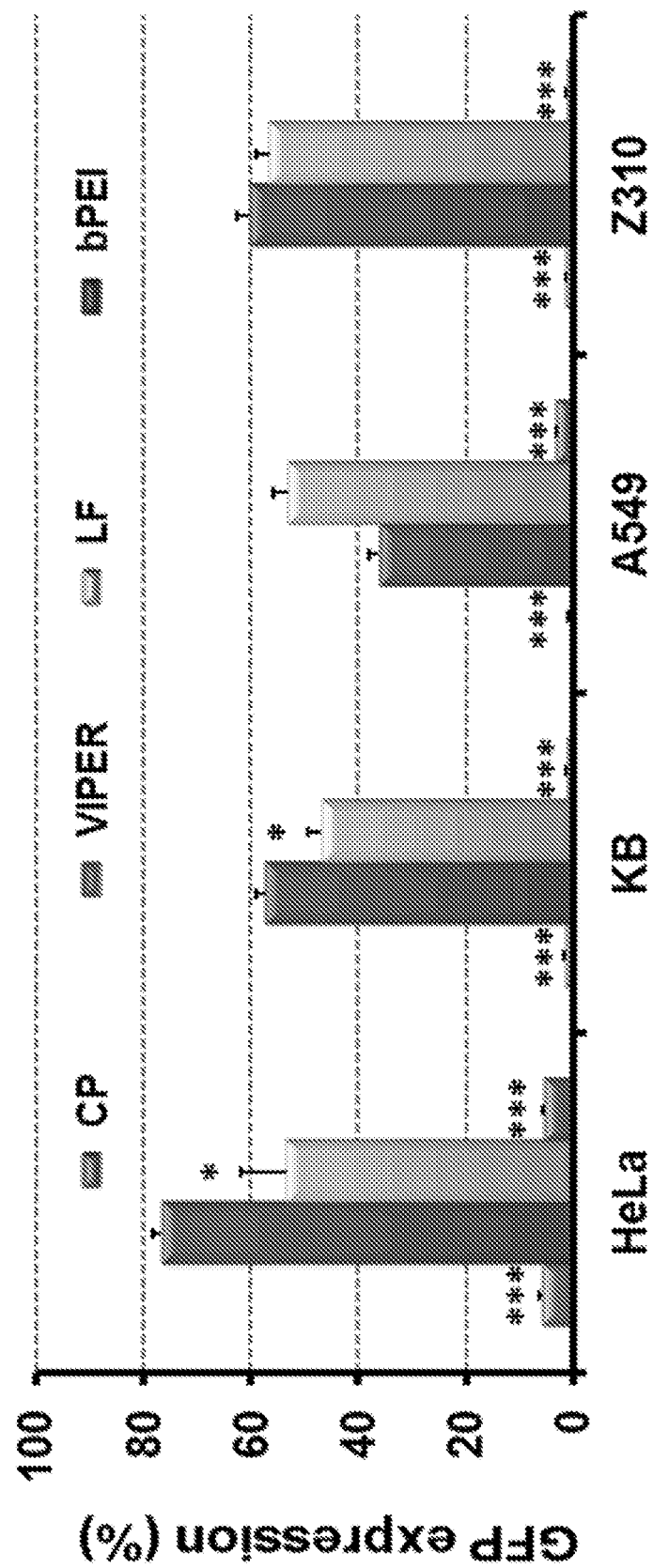
FIG. 3 shows the in vitro transfection of GFP plasmid to various immortalized cell lines using optimized formulations of VIPER/plasmid polyplexes. All the statistical analysis was performed compared to VIPER. Data are shown as mean±SD (n=3; student's t test, *p<0.05, ***p<0.001).

In order to address the dilemma of cytotoxicity versus transfection efficiency, the Wolff and Wagner groups developed masked melittin formulations, whereby melittin is reversibly blocked by maleic anhydride derivatives, rendering the peptide inactive at neutral pH and activated at acidic, endosomal pH by hydrolysis of the anhydride capping groups. M. Meyer et al. *Journal of the American Chemical Society* 2008, 130, 3272-3273; b) D. B. Rozema et al. *Bioconjugate Chemistry* 2003, 14, 51-57. The masked melittin materials mediated efficient delivery when co-injected with siRNA cholesterol, C. I. Wooddell et al. *Mol Ther* 2013, 21, 973-985 but polycations conjugated to melittin and siRNA showed liver toxicity when administered in vivo. M. Meyer et al. *Molecular Pharmaceutics* 2009, 6, 752-762. While effective, the anhydride protecting group is susceptible to hydrolysis, albeit at a reduced rate, even at physiological pH, which reduces stability and shelf-life of the material. In contrast, the membrane-lytic peptide in VIPER is masked by hydrophobic encapsulation within the micellar core until exposure by a pH-triggered switch in the block copolymer. Thus, the pH-sensitive polymer acts a responsive sheath to shield the "melittin sword". VIPER exhibits minimal membrane-lytic activity at pH 7.4, indicating efficient deactivation of melittin in neutral conditions, but becomes membrane-lytic in acidic environments (FIG. 2D). Accordingly, VIPER polyplexes could also efficiently escape endo/lysosomal compartments within 4 hours of internalization (FIG. 3).

VIPER also possesses other notable advances. First, the comonomer of OEGMA improves the stability of polyplexes, preventing salt-induced flocculation in physiological conditions, necessary for minimizing toxicity after in vivo administration (FIG. 6). Second, the pDIPAMA block not only acts as a shielding part for melittin deactivation, but also as an efficient method to enhance the stability of polyplexes. Hydrophobic modification of polycations has been demonstrated to improve blood circulation time and transfection efficiency compared to parent polycations while reducing the cytotoxicity and promoting the overall biodegradability of gene carriers. M. Thomas et al. *P Natl Acad Sci USA* 2002, 99, 14640-14645. The VIPERIDNA polyplexes did not show obvious size change in serum reduced medium compared to distilled water, and maintained their dimensions for 20 h (FIG. 6). Furthermore, intratumoral delivery studies demonstrated that VIPER polyplexes mediated much higher gene expression in tumor site compared to bPEI polyplexes (FIG. 3). Thus, the potential of VIPER for in vivo gene delivery may provide a useful platform for cancer therapy.

In summary, a virus-mimicking block copolymer that facilitates endosomal release, called VIPER, is disclosed. This polymer efficiently mediates both in vitro and in vivo gene transfer. The acid-triggered display of lytic peptide melittin effectively mediates endo/lysosomal escape of VIPER polyplexes, while masking melittin activity in extracellular conditions. VIPER therefore exhibits low cytotoxicity and potent endosomal escape properties and has strong potential as a delivery vehicle for macromolecular therapeutics.

EXPERIMENTAL SECTION

Materials.

2-(Dimethylamino)ethyl methacrylate (DMAEMA) and oligo(ethylene glycol) monomethyl ether methacrylate (OEGMA, $M_n$=300 and pendent EO units DP 4~5) were purchased from Sigma-Aldrich, and the monomers were purified by passing through a column filled with basic alumina to remove the inhibitor prior to polymerization. RAFT CTA 4-cyanopentanoic acid dithio-benzoate (CPADB), N,N'-Azobisisobutyronitrile (AIBN), anhydrous N,N'-dimethylacetamide (DMAc, HPLC, 99.9%) and dioxane were purchased from Sigma-Aldrich and used without further purification. Pyridyl disulfide ethyl methacrylate was synthesized as described previously. Meyer, C. et al. *Molecular Pharmaceutics* 2009. 2-Diisopropylaminoethyl methacrylate (DIPAMA) was purchased from Scientific Polymer Products Company and purified by passing through a basic alumina. Cysteine-melittin (Mel-cys; $NH_2$-GIGAVLKVLTTGLPALISWIKRKRQQCCONH$_2$) was prepared as our previous work.[16b] Endotoxin-free plasmid pCMV-Luc (Photinuspyralis luciferase under control of the cytomegalovirus (CMV) enhancer/promoter) was produced with the Qiagen Plasmid Giga kit (Qiagen, Hilden, Germany) according to the manufacturer's recommendations. YOYO-1 iodide and lipofectamine 2000 (LF) were purchased from Invitrogen (Carlsbad, Calif.).

Cell line. HeLa cells (ATCC CCL-2™) and KB cells (ATCC CCL-17) were maintained in minimum essential medium (MEM) supplemented with 10% fetal bovine serum (FBS) and antibiotics/antimyotics (AbAm) (100 IU of penicillin, 100 ug/mL of streptomycin, and 0.25 ug/mL of amphotericin B). A549 cells (ATCC CCL-185) were maintained in F-12K medium supplemented with 10% fetal bovine serum (FBS) and antibiotics/antimyotics (AbAm) (100 IU of penicillin, 100 ug/mL of streptomycin, and 0.25 ug/mL of amphotericin B). Z310 cells were donated by Prof. Wei Zheng (Purdue) and cultured in Dulbecco's minimum essential medium (DMEM) supplemented with 10% heat-inactivated FBS, 10% penicillin/streptomycin, 40 mg/mL gentamicin, and 10 ng/mL nerve growth factor (NGF).

Characterization.

$^1$H NMR spectra were recorded on a Bruker AV 300 (Bruker Corporation, Billerica, Mass.) nuclear magnetic resonance (NMR) instrument in deuterated chloroform ($CDCl_3$). The molecular weight and molecular weight distribution (PDI) of the polymers were determined by size exclusion chromatography. To prepare materials for analysis, the purified polymer was dissolved at 10 mg/ml in running buffer (0.15 M sodium acetate buffered to pH 4.4 with acetic acid) for analysis by SEC. Samples were then applied to an OHpak SB-804 HQ column (Shodex) in line with a miniDAWN TREOS light scattering detector (Wyatt) and a OptiLab rEX refractive index detector (Wyatt). Absolute molecular weight averages ($M_w$ and $M_n$) was calculated using ASTRA software (Wyatt).

Synthesis of p(OEGMA-DMAEMA).

The polymerization of OEGMA and DMAEMA by RAFT polymerization can be found anywhere. Thomas et al. *P Natl Acad Sci USA* 2002. In brief, OEGMA (1.0 g, 3.44 mmol), MAEMA (2.7 g, 17.2 mmol), AIBN (9.5 mg, 0.058 mmol) and CPADB (80 mg, 0.29 mmol) were dissolved in 5 mL dioxane. After purging with argon for 10 min, the reaction mixture was stirred in an oil bath at 60° C. for 18 h. The polymerization was quenched by immersing the reaction flask in liquid nitrogen. After thawing, the solution was precipitated in ether. The polymer was separated by centrifugation and further purified by redissolving/reprecipitating with DCM/ether three times.

Synthesis of p(OEGMA-DMAEMA)-b-p(DIPAMA-PDSEMA).

Block copolymer, p(OEGMA-DMAEMA)-b-p(DIPAMA-PDSEMA) was prepared using p(OEGMA-DMAEMA) as macro CTA. p($OEGMA_{11}$-$DMAEMA_{56}$) (80 mg, 0.0066 mmol), DIPAMA (282 mg, 1.32 mmol), PDSEMA (17 mg, 0.066 mmol) and AIBN (0.36 mg, 0.0022 mmol) were firstly dissolved 1.32 mL DMAc. After purging with argon for 5 min, the reaction solution was immersed in an oil bath at 60° C. After 30 min, the polymerization was quenched using liquid nitrogen. The polymer was purified by the dialysis against methanol for two days.

Conjugation of Cys-Melittin to p($OEGMA_{11}$-$DMAEMA_{56}$)-b-p($DIPAMA_{33}$-$PDSEMA_1$).

Cys-melittin was conjugated to the block copolymer through disulfide exchange reaction described as our previous work. Meyer, C. et al. *Molecular Pharmaceutics* 2009. p($OEGMA_{11}$-$DMAEMA_6$)-b-p($DIPAMA_{33}$-$PDSEMA_1$) (20 mg, 0.001 mmol PDS groups) was dissolved in 2 mL PB buffer (0.2 M, pH 5.7) in a 10 mL flask. Then, 6.1 mg (0.002 mmol, 2 equiv relative to PDS groups) of cys-melittin was added into the flask and allowed to stir under argon at room temperature. The reaction was monitored by UV at 340 nm for the release of 2-thio-pyridine. After 20 h, the absorption was saturated and the reaction mixture was passed through a PD-10 column to remove the side product and unreacted peptide followed by lyophilization. The characterization of the copolymers is presented in Table 1.

TABLE 1

|  |  | $M_n{}^a$ | $M_n{}^b$ | $PDI^b$ |
|---|---|---|---|---|
| macroCTA | P($OEGMA_{11}$-$DMAEMA_{56}$) | 15,300 | 17,600 | 1.04 |
| CP | P($OEGMA_{11}$-$DMAEMA_{56}$)-b-p($DIPAMA_{33}$-$PDSEMA)_1$ | 19,100 | 21,400 | 1.03 |
| VIPER | P($OEGMA_{11}$-$DMAEMA_{56}$)-b-p($DIPAMA_{33}$-$PDSEMA$-g-$melittin)_1$) | 22,800 | 24,900 | 1.03 |

[a]Determined by $^1$H NMR;
[b]Obtained by GPC.

Hemolysis of Polymers.

Hemolysis assay was used to evaluate the acid-triggered membrane-lytic activity of the synthesized materials at pH 7.4 (extracellular pH) and 5.7 (endosomal pH). Briefly, plasma from human blood was removed by centrifugation. The red blood cells were washed three times with 150 mM NaCl, and resuspended into phosphate buffer (PB) at pH 7.4 or 5.7. The polymers at various concentrations (7.5-240 pg/mL) and 1% Triton X-100 as control, were added to the RBC suspensions in a 96-well conical plate and was allowed to incubate for 1 h at 37° C. After centrifugation, the released hemoglobin within the supernatant was measured by UV at 541 nm. Percent hemolysis was calculated relative to Triton X-100. Experiments were performed in triplicate.

Preparation and Characterization of DNA Polyplexes.

The polymer/DNA polyplexes was formed by adding polymer to DNA solution followed by 30 min incubation at room temperature. For the gel retardation study, the polyplexes with various N/P ratios were loaded onto a 1% agarose gel containing TAE buffer (40 μmM tris-acetate, 1 mM EDTA) and 5 mg/mL ethidium bromide, and were electrophoresed at 100 V for 40 min. The pDNA was then visualized using a Kodak (Rochester. NK) UV transilluminator (laser-excited fluorescence gel scanner).

The size and surface charge of the polyplexes were tested on a ZetaPLUS instrument (Brookhaven Instruments Corporation, Holtsvile, N.Y.). The samples were prepared by mixing polyplexes (1 μg DNA, 20 μL solution, N/P=5) with 800 μL ddH$_2$O. The measurements were performed in triplicate.

Transmission Electron Microscope (TEM).

The morphology of polymers and polyplexes under dried state were imaged on a JEOL 1140 TEM at an acceleration voltage of 100 kV. In order to observe the morphology of polymer assemblies under different pHs, the polymer solutions (1 mg/mL, in distilled water) were diluted with PB to pH 7.4 and 5.7. Then the resulting solutions (10 μL) were deposited on the top of the 400-mesh formvar/copper grids and incubated at room temperature for 30 min. After staining with uranyl acetate, the grids were allowed to air dry overnight. The preparation of polyplexes samples were the same as polymer samples.

In Vitro Cell Studies.

Transfection in Immortalized/Cancer Cells.

HeLa, KB, Z310 and A549 cells were seeded at a density of 25,000 cells/well in complete cell culture medium in a 24-well plate. Cells were firstly incubated at 37° C., 5% CO$_2$ for 24 h. Polyplexes were prepared at different N/P ratios using 0.5 μg of pCMV-Luc2 pDNA in 10 μL total volume. Each sample was diluted to 200 μL with complete cell culture medium. The cells were rinsed once with PBS, followed by the addition of transfection solution. After incubation for 4 h, cells were washed with PBS twice and the polyplexes solution was replaced with complete cell culture medium. After additional 20 h incubation, luciferase activity was quantified with a luciferase assay kit (Promega Corp, Fitchburg, Wis.) according to the manufacturer's instruction, except that a freeze-thaw cycle at −80 OC was included after the addition of the lysis buffer to ensure complete cell lysis. Luminescence intensity was measured on the plate reader with integration for 1 s. The total protein content in each well was measured by a BCA Protein Assay Kit (Thermo Scientific, Rockford, Ill.) according to the manufacturer's instruction so that the luciferase activity was normalized to the total protein content in each well. Each sample was tested with a sample size (n)=3. The N/P ratio used for bPEI is 5, which was previous determined to show optimized transfection efficiency. LF was used according to the manufacturer's instruction in serum-free media.

GFP Transfection.

The transfection with GFP (green fluorescence plasmid) on different cell lines was the same as that with luciferase plasmid. For analysis, cells were washed with PBS, trypsinized and pelleted at 300×g for 5 min at 4° C. The pellet was resuspended in 0.3 mL propidium iodide (PI) solution (1 μg/mL in 0.5% BSA in PBS), kept on ice and analyzed using flow cytometry, MACSQuant Analyzer (Miltenyi Biotec Inc., Auburn, Calif.). Intact cells were identified using the forward and side scatter data. The resulting cell population was gated into GFP+/PI+, GFP+/PI−, GFP−/PI+ and GFP−/PI− based on the green fluorescence and PI intensity from the control samples (cells transfected without the polymers but DNA only) and reported as the mean percentage of cell population that is GFP+/PI− including standard deviation (SD). All experiments were conducted in triplicate.

Endosomal Escape of Polyplexes by Confocal Microscope.

To evaluate the endosomal escape ability of melittin-polymer based polyplexes, DNA was firstly labeled with YOYO-1. The cells were incubated with polyplexes for 4 h. The acidic vesicles and the nuclei of cells were stained with LysoTracker Red, DND-99 and 4',6-diamidino-2-phenylindole (DAPI), respectively. To quantify the endosomal escape ratio of polyplexes, the colocalization ratio between DNA and LysoTracker Red was quantified as follows using Image J software:

$$\text{Colocalization ratio (\%)} = \frac{YOYO-1 \text{ pixels}_{colocalization}}{YOYO-1 \text{ pixels}_{total}} \times 100\%$$

Where YOYO-1 pixels$_{co\text{-}localization}$ represents the number of YOYO-1 pixels co-localizing with Lysotracker Red, and YOYO-1 pixels$_{total}$ represents the number of all YOYO-1 pixels in the confocal images. Results were presented as the mean of 15 individual cells.

Intra-Tumoral Gene Delivery.

All animal procedures were done using protocols approved by the Institutional Animal Care and Use Committee at the University of Washington. For A549 tumor inoculation, 100 μL of A549 cell suspensions (2.0×10$^6$ cells in F12 medium) were subcutaneously injected into female Scid-beige (CBI7) mice (4-5 week old). When the tumor size reached 100 mm$^3$, 50 μL polyplexes (CP/DNA, VIPER/DNA, bPEI/DNA) in 5% glucose solution (containing 10 μg luciferase plasmid) were injected into mice. The administrations for every mouse were repeated for three days. At the fourth day, 200 μL D-luciferin potassium salts (15 mg/mL) was intraperitoneally injected into the mice. A 5 min post-injection, the mice were placed into an in vivo imaging system (Xenogen IVIS-200, Caliper Life Sciences, Hopkinton), and the luminescence at tumor site was recorded with an exposure time of 2 min. The tumor tissues were harvested from mice and collected in lysis buffer supplemented by protease inhibitors (Roche, Nutley, N.J.) and three freeze thaw cycles were performed in liquid nitrogen. Tissues were mechanically homogenized and lysate was cleared by spinning at 21,000 g for 15 min at 4° C. 20 pL of lysate was assayed for luminescence with 100 μL of luciferase substrate. Luminescence was measured and normalized by protein content in the three brain sections, determined using a BCA Protein Assay Kit (Pierce), and reported as relative light units (RLU) per mg brain.

Statistical Analysis.

All statistical analyses were performed using a two-tailed Student's t-test with unequal variance.

Synthesis of Example Copolymer

A carboxyl functionalized chain transfer agent was used to prepare functional polymer for targeted peptide delivery by reversible addition-fragmentation chain transfer (RAFT) polymerization. The hydrophilic block, poly(oligo(ethylene glycol) monomethyl ether methacrylate)-co-poly(pyridyl disulfide ethyl methacrylate) (p(OEGMA-PDSEMA)), includes PDSEMA, used for thiol-containing peptide cargo conjugation through disulfide exchange reaction, and OEGMA, a hydrophilic monomer to provide colloidal stability. The pH-sensitive block, poly(2-diisopropylaminoethyl methacrylate)-co-poly(2-azidoethyl methacrylate) (p(DIPAMA-AEMA)), includes p(DIPAMA)), a pH sensitive polymer which features a sharp phase transition from hydrophobic to hydrophilic at pH 6.3, and AEMA monomers to enable further fimctionalization with alkynyl-containing lytic peptides through click chemistry. The terminal carboxyl group can be used for the targeting group conjugation through NHS chemistry (Scheme 2).

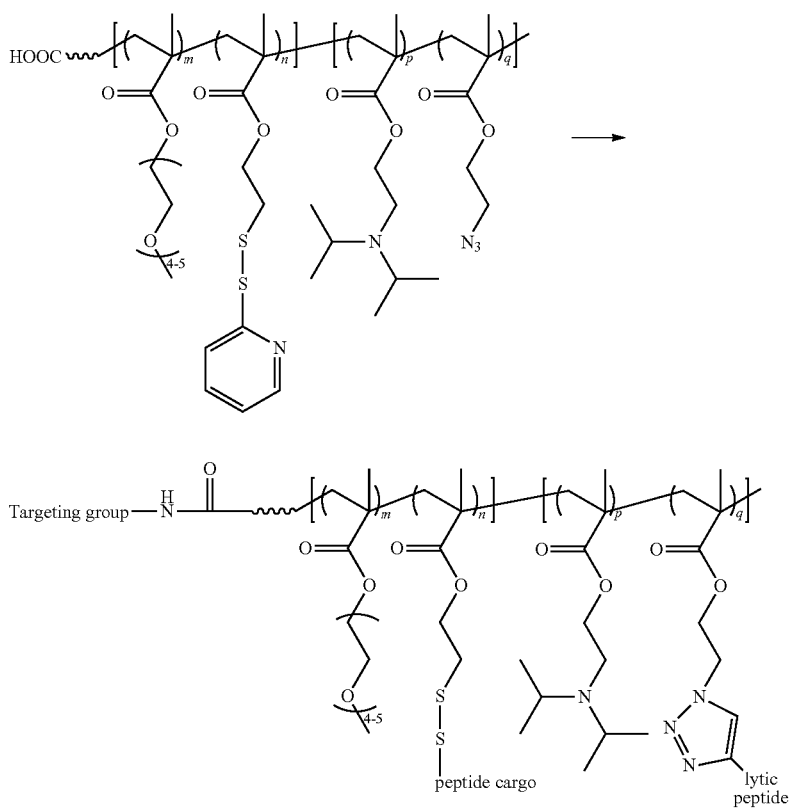

Scheme 2

A carboxyl functionalized chain transfer agent was used to prepare functional polymer for targeted peptide delivery by reversible addition-fragmentation chain transfer (RAFT) polymerization. The hydrophilic block, poly(oligo(ethylene glycol) monomethyl ether methacrylate (p(OEGMA)), includes OEGMA, a hydrophilic monomer to provide colloidal stability. The pH-sensitive block, poly(2-diisopropylaminoethyl methacrylate)-co-poly(2-azidoethyl methacrylate)-co-poly(pyridyl disulfide ethyl methacrylate) (p(DIPAMA-AEMA-PDSEMA)), includes p(DIPAMA)), a pH sensitive polymer which features a sharp phase transition from hydrophobic to hydrophilic at pH 6.3, AEMA monomers to enable further functionalization with alkynyl-containing lytic peptides through click chemistry, and PDSEMA, used for thiol-containing peptide cargo conjugation through disulfide exchange reaction The terminal carboxyl group can be used for the targeting group conjugation through NHS chemistry (Scheme 3).

Scheme 3

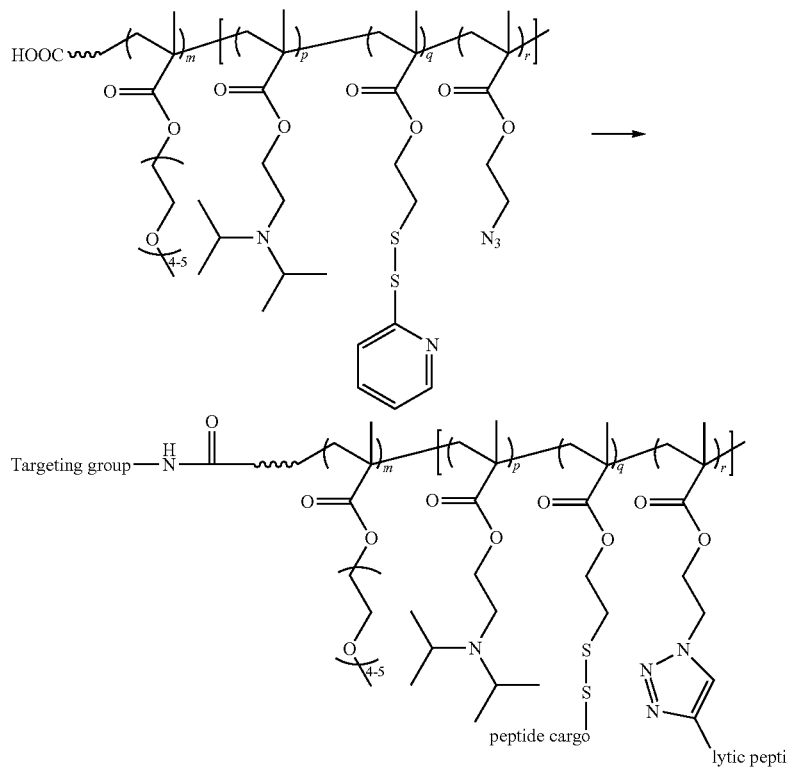

What is claimed:

1. A block copolymer of formula (II):

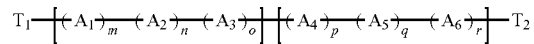

wherein
each $A_1$ is a hydrophilic monomer-derived unit,
each $A_2$ is a monomer-derived unit that is either independently neutral or charged at pH 10 or less;
each $A_3$ is a monomer-derived unit including a therapeutic agent;
each $A_4$ is a monomer-derived unit with a pKa ranging from about pH 4 to about pH 7;
each $A_5$ is a monomer-derived unit including a therapeutic agent;
$A_6$ is a monomer-derived unit including a membrane-lytic peptide;
$T_1$ is absent or a targeting group;
$T_2$ is absent, a membrane-lytic peptide, or a therapeutic agent;
m is from 1 to about 10,000;
n is from 0 to about 10,000;
o is from 0 to about 10,000;
p is from 1 to about 10,000;
q is from 0 to about 10,000; and
r is from 1 to about 10,000.

2. The block copolymer of claim 1, wherein $A_1$, $A_2$ or $A_3$ independently comprise repeating units derived from a monomer selected from the group consisting of 2-(dimethylamino)ethyl methacrylate, 2-dimethylaminoethyl acrylate, (3-acrylamidopropyl)trimethylammonium chloride, N-(3-aminopropyl) methacrylamide, N,N-diethylacrylamide, N,N-diethylmethacrylamide, N,N-dimethylacrylamide, N-[3-(dimethylamino)propyl]methacrylamide, 2-aminoethyl methacrylate, 2-(diethylamino)ethyl methacrylate, 2-(dimethylamino)ethylmethacrylate, [2-hydroxy-3-(2-aminoethyl)amino]propyl methacrylate, [3-methacryloylamino)propyl]trimethylammonium chloride, and L-lysine.

3. The block copolymer of claim 1, wherein $A_1$, $A_2$ or $A_3$ independently comprise repeating units derived from a monomer selected from the group consisting of methacrylic acid, acrylic acid, dimethylmaleic anhydride modified N-(3-aminopropyl) methacrylamide, and 2-aminoethyl methacrylate.

4. The block copolymer of claim 1, wherein $A_1$, $A_2$ or $A_3$ independently comprise repeating units derived from a monomer selected from the group consisting of oligo(ethylene glycol), hydroxypropylmethacrylamide, 2-hydroxyethyl methacrylate, N-isopropylacrylamide, 3-glucanoamidopropyl methacrylamide, 2-lactobionamidoethyl methacrylamide, betaine, phosphocholine, sulfobetaine and carboxybetaine.

5. The block copolymer of claim 1, wherein $A_4$, $A_5$ or $A_6$ independently comprise repeating units derived from a monomer selected from the group consisting of 2-diisopropylaminoethyl methacrylate, 2-(pentamethyleneimino)ethyl methacrylate, 2-(hexamethyleneimino)ethyl methacrylate, 2-(dipropylamino) ethyl methacrylate, 2-(dibutylamino) ethyl methacrylate, 2-(dipentylamino) ethyl methacrylate and 2-(ethylpropylamino) ethyl methacrylate.

6. The block copolymer of claim 1, wherein the membrane-lytic peptide is covalently linked to $A_6$ through a linker.

7. The block copolymer of claim 6, wherein the linker is selected from a carbon-carbon bond, an oligonucleotide, an ester-containing fragment, an amide-containing fragment or a disulfide-containing fragment.

8. The block copolymer of claim 6, wherein the linker is a disulfide bridge.

9. The block copolymer of claim 1, wherein the membrane-lytic peptide is selected from the group consisting of melittin, peptides from adeno virus protein VI, GALA, KALA, EGLA, JTS1, Gramicidin S, HGP peptide (sequence LLGRRGWEVLKYWWNLLQYWSQEL) (SEQ ID NO:1), sHGP peptide (sequence RGWEVLKYWWNLLQY) (SEQ ID NO:2), TAT peptide (sequence GRKKRRQRRRPQ) (SEQ ID NO:3), oligoarginine, CaLL (KWKLFKKIFKRIVQRIKDFLR) (SEQ ID NO:4), hadrurin (GILDTIKSIASKVWNSKTVQDLKRKGINWVANKLGVSPQAA) (SEQ ID NO:5), cupiennin 1a (GFGALFKFLAKKVAKT-VAKQAAKQGAKYVVNKQME) (SEQ ID NO:6), crabolin (Fmoc-FLALILRKIVTAL-CONH2) (SEQ ID NO:7), IsCT (ILGKIWEGIKSLF-NH2) (SEQ ID NO:8), HsAP (SGTSEKERESGRLLGVVKRLIVCFRSPFP-NH2) (SEQ ID NO:9), Pandinin2 (FWGALAKGALKLIPSLF-SSFSKKD) (SEQ ID NO:10), Ponericin (WLGSALKI-GAKLLPSVVGLFKKKKQ) (SEQ ID NO:11), UyCT5 (IWSAIWSGIKGLL-NH2) (SEQ ID NO:12) and hemagglutinin.

10. The block copolymer of claim 1, having the structure of Formula (IIa):

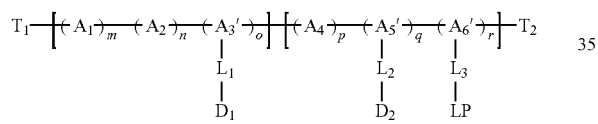

(IIa)

wherein each $A_1$ is a hydrophilic monomer-derived unit, each $A_2$ is a monomer-derived unit that is neutral or charged at pH of 10.0 or less;

each $A_4$ is a monomer-derived unit with a pKa ranging from about pH 4 to about pH 7;

each $A_3'$, $A_5'$ and $A_6'$ is independently

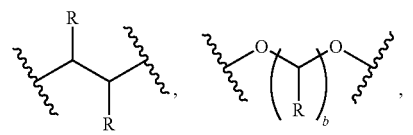

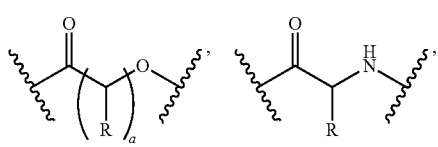

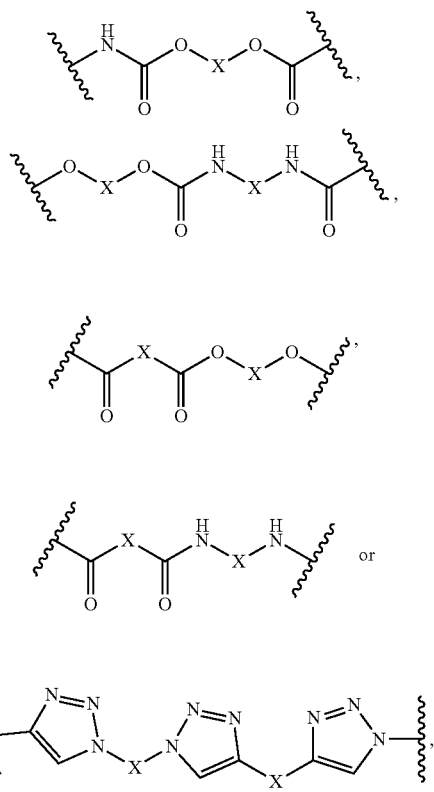

wherein each X independently comprises repeating units comprising an alkylene, arylene, disulfide, alkylene oxide or propane-2,2-diol;

wherein each X is optionally substituted with —$CO_2R^1$, $L_1$-$D_1$, $L_2$-$D_2$ or, $L_3$-LP, wherein $R^1$ is a hydrophilic group, each R is independently hydrogen, —$CO_2R^2$, —CN, alkyl, alkynyl, heteroalkyl, cycloalkyl, heterocycloalkyl, aryl or heteroaryl, where $R^2$ is a hydrophilic group, $L_1$-$D_1$, $L_2$-$D_2$ or $L_3$-LP, a is 1-4, and b is 2-4;

each of $L_1$, $L_2$ and $L_3$ is independently absent or a linker;

each LP is a membrane-lytic peptide;

each of $D_1$ and $D_2$ is independently a therapeutic agent;

$T_1$ is absent or a targeting group;

$T_2$ is absent, a membrane-lytic peptide, a therapeutic agent;

m is from 1 to about 10,000;

n is from 0 to about 10,000;

o is from 0 to about 10,000;

p is from 1 to about 10,000;

q is from 0 to about 10,000; and r is from 1 to about 10,000.

11. The block copolymer of claim 10, having the structure of Formula (IIIb):

(IIIb)

[structural formula IIIb]

wherein m' is from 1 to about 20.

12. The block copolymer of claim 10, having the structure of Formula (IVb):

(IVb)

[structural formula IVb]

wherein m' is from about 1 to about 20; and each R' is independently hydrogen, alkyl, cycloalkyl, heterocycloalkyl, aryl, alkyl-cycloalkyl, alkyl-heterocycloalkyl or alkyl-aryl.

13. A micellar assembly comprising a plurality of copolymers according to claim 1.

14. A pharmaceutical composition comprising:
at least one block copolymer according to claim 1; and
a therapeutic agent reversibly associated with at least one of $A_1$, $A_2$ or $A_3$.

15. A method of intracellularly delivering a therapeutic agent comprising:
administering a pharmaceutical composition according to claim 14 to a subject, wherein the pharmaceutical composition is endocytosed into the endosome and the pharmaceutical composition, thereby, releases the therapeutic agent into the endosome.

16. A block copolymer of formula (II):

(II)

$$T_1-[(A_1)_m-(A_2)_n-(A_3)_o]-[(A_4)_p-(A_5)_q-(A_6)_r]-T_2$$

wherein
each $A_1$ is a hydrophilic monomer-derived unit,
each $A_2$ is a monomer-derived unit that is either independently neutral or charged at pH 10 or less;
each $A_3$ is a monomer-derived unit including a therapeutic agent;
each $A_4$ is a monomer-derived unit with a pKa ranging from about pH 4 to about pH 7;
each $A_5$ is a monomer-derived unit including a therapeutic agent;
$A_6$ is a monomer-derived unit including a membrane-lytic peptide;
$T_1$ is absent or a targeting group;
$T_2$ is a membrane-lytic peptide;
m is from 1 to about 10,000;
n is from 0 to about 10,000;
o is from 0 to about 10,000;
p is from 1 to about 10,000;
q is from 0 to about 10,000; and
r is from 0 to about 10,000.

17. The block copolymer of claim 16, wherein the membrane-lytic peptide is selected from the group consisting of melittin, peptides from adeno virus protein VI, GALA, KALA, EGLA, JTS1, Gramicidin S, HGP peptide (sequence LLGRRGWEVLKYWWNLLQYWSQEL) (SEQ ID NO:1), sHGP peptide (sequence RGWEVLKYWWNLLQY) (SEQ ID NO:2), TAT peptide (sequence GRKKRRQRRRPQ) (SEQ ID NO:3), oligoarginine, CaLL (KWKLFKKIFKRIVQRIKDFLR) (SEQ ID NO:4), hadrurin (GILDTIKSIASKVWNSKTVQDLKRKGINWVANKLGVSPQAA) (SEQ ID NO:5), cupiennin 1a (GFGALFKFLAKKVAKT-VAKQAAKQGAKYVVNKQME) (SEQ ID NO:6), crabolin (Fmoc-FLALILRKIVTAL-CONH2) (SEQ ID NO:7), IsCT (ILGKIWEGIKSLF-NH2) (SEQ ID NO:8), HsAP (SGTSEKERESGRLLGVVKRLIVCFRSPFP-NH2) (SEQ ID NO:9), Pandinin2 (FWGALAKGALKLIPSLF-SSFSKKD) (SEQ ID NO:10), Ponericin (WLGSALKI-GAKLLPSVVGLFKKKKQ) (SEQ ID NO:11), UyCT5 (IWSAIWSGIKGLL-NH2) (SEQ ID NO:12) and hemagglutinin.

18. A micellar assembly comprising a plurality of copolymers according to claim 16.

19. A pharmaceutical composition comprising:
at least one block copolymer according to claim 16; and
a therapeutic agent reversibly associated with at least one of $A_1$, $A_2$ or $A_3$.

20. A method of intracellularly delivering a therapeutic agent comprising:
administering a pharmaceutical composition according to claim 19 to a subject, wherein the pharmaceutical composition is endocytosed into the endosome and the pharmaceutical composition, thereby, releases the therapeutic agent into the endosome.

21. A block copolymer of formula (II):

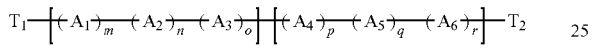

(II)

wherein
each $A_1$ is a hydrophilic monomer-derived unit, each $A_2$ is a monomer-derived unit that is either independently neutral or charged at pH 10 or less;
each $A_3$ is a monomer-derived unit including a therapeutic agent;
each $A_4$ is a monomer-derived unit with a pKa ranging from about pH 4 to about pH 7;
each $A5$ is a monomer-derived unit including a therapeutic agent;
$A_6$ is a monomer-derived unit including a membrane-lytic entity;
$T_1$ is absent or a targeting group;
$T_2$ is absent, a membrane-lytic entity, or a therapeutic agent;
m is from 1 to about 10,000;
n is from 0 to about 10,000;
o is from 0 to about 10,000;
p is from 1 to about 10,000;
q is from 0 to about 10,000; and
r is from 1 to about 10,000,
wherein the membrane-lytic entity is selected from the group consisting of melittin, peptides from adeno virus protein VI, GALA, KALA, EGLA, JTS1, Gramicidin S, HGP peptide (sequence LLGRRGW-EVLKYWWNLLQYWSQEL) (SEQ ID NO:1), sHGP peptide (sequence RGWEVLKYWWNLLQY) (SEQ ID NO:2), TAT peptide (sequence GRKKRRQRRRPQ) (SEQ ID NO:3), oligoarginine, CaLL (KWKLFKKIFKRIVQRIKDFLR) (SEQ ID NO:4), hadrurin (GILDTIK-SIASKVWNSKTVQDLKRKGINW-VANKLGVSPQAA) (SEQ ID NO:5), cupiennin 1a (GFGALFKFLAKKVAKT-VAKQAAKQGAKYVVNKQME) (SEQ ID NO:6), crabolin (Fmoc-FLALILRKIVTAL-CONH2) (SEQ ID NO:7), IsCT (ILGKIWEGIKSLF-NH2) (SEQ ID NO:8), HsAP (SGTSEKERES-GRLLGVVKRLIVCFRSPFP-NH2) (SEQ ID NO:9), Pandinin2 (FWGALAKGALKLIPSLFSSFSKKD) (SEQ ID NO:10), Ponericin (WLGSALKIGAK-LLPSVVGLFKKKKQ) (SEQ ID NO:11), UyCT5 (IWSAIWSGIKGLL-NH2) (SEQ ID NO:12) and hemagglutinin.

* * * * *

SEQUENCE LISTING

<160> NUMBER OF SEQ ID NOS: 13

<210> SEQ ID NO 1
<211> LENGTH: 24
<212> TYPE: PRT
<213> ORGANISM: Artificial Sequence
<220> FEATURE:
<223> OTHER INFORMATION: HGP peptide

<400> SEQUENCE: 1

Leu Leu Gly Arg Arg Gly Trp Glu Val Leu Lys Tyr Trp Trp Asn Leu
1               5                   10                  15

Leu Gln Tyr Trp Ser Gln Glu Leu
            20

<210> SEQ ID NO 2
<211> LENGTH: 15
<212> TYPE: PRT
<213> ORGANISM: Artificial Sequence
<220> FEATURE:
<223> OTHER INFORMATION: sHGP peptide

<400> SEQUENCE: 2

Arg Gly Trp Glu Val Leu Lys Tyr Trp Trp Asn Leu Leu Gln Tyr
1               5                   10                  15

<210> SEQ ID NO 3
<211> LENGTH: 12
<212> TYPE: PRT
<213> ORGANISM: Artificial Sequence
<220> FEATURE:

```
<223> OTHER INFORMATION: TAT peptide

<400> SEQUENCE: 3

Gly Arg Lys Lys Arg Arg Gln Arg Arg Arg Pro Gln
1               5                   10

<210> SEQ ID NO 4
<211> LENGTH: 21
<212> TYPE: PRT
<213> ORGANISM: Artificial Sequence
<220> FEATURE:
<223> OTHER INFORMATION: CaLL

<400> SEQUENCE: 4

Lys Trp Lys Leu Phe Lys Lys Ile Phe Lys Arg Ile Val Gln Arg Ile
1               5                   10                  15

Lys Asp Phe Leu Arg
            20

<210> SEQ ID NO 5
<211> LENGTH: 41
<212> TYPE: PRT
<213> ORGANISM: Artificial Sequence
<220> FEATURE:
<223> OTHER INFORMATION: hadrurin

<400> SEQUENCE: 5

Gly Ile Leu Asp Thr Ile Lys Ser Ile Ala Ser Lys Val Trp Asn Ser
1               5                   10                  15

Lys Thr Val Gln Asp Leu Lys Arg Lys Gly Ile Asn Trp Val Ala Asn
            20                  25                  30

Lys Leu Gly Val Ser Pro Gln Ala Ala
        35                  40

<210> SEQ ID NO 6
<211> LENGTH: 35
<212> TYPE: PRT
<213> ORGANISM: Artificial Sequence
<220> FEATURE:
<223> OTHER INFORMATION: cupiennin 1a

<400> SEQUENCE: 6

Gly Phe Gly Ala Leu Phe Lys Phe Leu Ala Lys Lys Val Ala Lys Thr
1               5                   10                  15

Val Ala Lys Gln Ala Ala Lys Gln Gly Ala Lys Tyr Val Val Asn Lys
            20                  25                  30

Gln Met Glu
        35

<210> SEQ ID NO 7
<211> LENGTH: 13
<212> TYPE: PRT
<213> ORGANISM: Artificial Sequence
<220> FEATURE:
<223> OTHER INFORMATION: crabolin
<220> FEATURE:
<221> NAME/KEY: MISC_FEATURE
<222> LOCATION: (1)..(1)
<223> OTHER INFORMATION: N-terminus fluorenylmethyloxycarbonyl group
<220> FEATURE:
<221> NAME/KEY: MISC_FEATURE
<222> LOCATION: (13)..(13)
<223> OTHER INFORMATION: C-terminus amide group

<400> SEQUENCE: 7
```

Phe Leu Ala Leu Ile Leu Arg Lys Ile Val Thr Ala Leu
1               5                   10

<210> SEQ ID NO 8
<211> LENGTH: 13
<212> TYPE: PRT
<213> ORGANISM: Artificial Sequence
<220> FEATURE:
<223> OTHER INFORMATION: IsCT
<220> FEATURE:
<221> NAME/KEY: MISC_FEATURE
<222> LOCATION: (13)..(13)
<223> OTHER INFORMATION: C-terminus amine group

<400> SEQUENCE: 8

Ile Leu Gly Lys Ile Trp Glu Gly Ile Lys Ser Leu Phe
1               5                   10

<210> SEQ ID NO 9
<211> LENGTH: 29
<212> TYPE: PRT
<213> ORGANISM: Artificial Sequence
<220> FEATURE:
<223> OTHER INFORMATION: HsAP
<220> FEATURE:
<221> NAME/KEY: MISC_FEATURE
<222> LOCATION: (29)..(29)
<223> OTHER INFORMATION: C-terminus amine group

<400> SEQUENCE: 9

Ser Gly Thr Ser Glu Lys Glu Arg Glu Ser Gly Arg Leu Leu Gly Val
1               5                   10                  15

Val Lys Arg Leu Ile Val Cys Phe Arg Ser Pro Phe Pro
            20                  25

<210> SEQ ID NO 10
<211> LENGTH: 24
<212> TYPE: PRT
<213> ORGANISM: Artificial Sequence
<220> FEATURE:
<223> OTHER INFORMATION: Pandinin2

<400> SEQUENCE: 10

Phe Trp Gly Ala Leu Ala Lys Gly Ala Leu Lys Leu Ile Pro Ser Leu
1               5                   10                  15

Phe Ser Ser Phe Ser Lys Lys Asp
            20

<210> SEQ ID NO 11
<211> LENGTH: 25
<212> TYPE: PRT
<213> ORGANISM: Artificial Sequence
<220> FEATURE:
<223> OTHER INFORMATION: Ponericin

<400> SEQUENCE: 11

Trp Leu Gly Ser Ala Leu Lys Ile Gly Ala Lys Leu Leu Pro Ser Val
1               5                   10                  15

Val Gly Leu Phe Lys Lys Lys Lys Gln
            20                  25

<210> SEQ ID NO 12
<211> LENGTH: 13
<212> TYPE: PRT
<213> ORGANISM: Artificial Sequence
<220> FEATURE:
<223> OTHER INFORMATION: UyCT5

```
-continued

<220> FEATURE:
<221> NAME/KEY: MISC_FEATURE
<222> LOCATION: (13)..(13)
<223> OTHER INFORMATION: C-terminus amine group

<400> SEQUENCE: 12

Ile Trp Ser Ala Ile Trp Ser Gly Ile Lys Gly Leu Leu
1               5                   10

<210> SEQ ID NO 13
<211> LENGTH: 27
<212> TYPE: PRT
<213> ORGANISM: Artificial Sequence
<220> FEATURE:
<223> OTHER INFORMATION: Cysteine-melittin
<220> FEATURE:
<221> NAME/KEY: MISC_FEATURE
<222> LOCATION: (27)..(27)
<223> OTHER INFORMATION: C-terminus amide group

<400> SEQUENCE: 13

Gly Ile Gly Ala Val Leu Lys Val Leu Thr Thr Gly Leu Pro Ala Leu
1               5                   10                  15

Ile Ser Trp Ile Lys Arg Lys Arg Gln Gln Cys
            20                  25
```